(12) United States Patent
Mansour et al.

(10) Patent No.: US 11,878,023 B2
(45) Date of Patent: Jan. 23, 2024

(54) COMPOSITIONS AND METHODS FOR DELIVERING PHARMACEUTICAL AGENTS

(71) Applicant: Arizona Board of Regents on Behalf of the University of Arizona, Tucson, AZ (US)

(72) Inventors: Heidi M. Mansour, Tucson, AZ (US); Stephen Black, Tucson, AZ (US); Priyadarshini Muralidharan, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 324 days.

(21) Appl. No.: 16/759,102

(22) PCT Filed: Oct. 25, 2018

(86) PCT No.: PCT/US2018/057551
§ 371 (c)(1),
(2) Date: Apr. 24, 2020

(87) PCT Pub. No.: WO2019/084293
PCT Pub. Date: May 2, 2019

(65) Prior Publication Data
US 2021/0177860 A1  Jun. 17, 2021

Related U.S. Application Data

(60) Provisional application No. 62/576,957, filed on Oct. 25, 2017.

(51) Int. Cl.

| | | |
|---|---|---|
| *A61K 31/551* | (2006.01) | |
| *A61K 9/00* | (2006.01) | |
| *A61K 9/50* | (2006.01) | |
| *A61K 9/51* | (2006.01) | |
| *A61K 45/06* | (2006.01) | |
| *A61K 47/26* | (2006.01) | |

(52) U.S. Cl.
CPC .......... *A61K 31/551* (2013.01); *A61K 9/0075* (2013.01); *A61K 9/5089* (2013.01); *A61K 9/5192* (2013.01); *A61K 45/06* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 5,942,505 | A | 8/1999 | Kawakubo et al. |
| 6,766,799 | B2 | 7/2004 | Edwards et al. |
| 6,848,197 | B2 | 2/2005 | Chen et al. |
| 7,278,425 | B2 | 10/2007 | Edwards et al. |
| 8,197,845 | B2 | 6/2012 | Hartig et al. |
| 8,496,002 | B2 | 7/2013 | Ellwanger et al. |
| 2004/0204500 | A1 | 10/2004 | Sugiyama et al. |
| 2006/0280793 | A1 | 12/2006 | Sugi et al. |

FOREIGN PATENT DOCUMENTS

| | | | |
|---|---|---|---|
| CN | 101601654 | | 8/2010 |
| JP | 2005206485 | A * | 8/2005 |
| WO | WO 2016/073836 | | 5/2016 |

OTHER PUBLICATIONS

Rahimpour et al. (Drug Discovery Today, 19 (5):618-626, 2014).*
Acosta, MF, et al., In Vitro Pulmonary Cell Culture in Pharmaceutical Inhalation Aerosol Delivery: 2-D, 3-D, and In Situ Bioimpactor Models. Curr Pharm Des. 2016;22(17):2522-31.
Amano, M, et al., Rho-kinase/ROCK: A key regulator of the cytoskeleton and cell polarity. Cytoskeleton (Hoboken). Sep. 2010;67(9):545-54.
Ding, RY, et al., Pretreatment of Rho kinase inhibitor inhibits systemic inflammation and prevents endotoxin-induced acute lung injury in mice. J Surg Res. Dec. 2011; 171(2):e209-14.
Duan, J, et al., Design, characterization, and aerosolization of organic solution advanced spray-dried moxifloxacin and ofloxacin dipalmitoylphosphatidylcholine (DPPC) microparticulate/nanoparticulate powders for pulmonary inhalation aerosol delivery. Int J Nanomedicine. 2013;8:3489-505.
Galie, N, et al., 2015 ESC/ERS Guidelines for the diagnosis and treatment of pulmonary hypertension: The Joint Task Force for the Diagnosis and Treatment of Pulmonary Hypertension of the European Society of Cardiology (ESC) and the European Respiratory Society (ERS): Endorsed by: Association for European Paediatric and Congenital Cardiology (AEPC), International Society for Heart and Lung Transplantation (ISHLT). Eur Respir J. Oct. 2015;46(4):903-75.
Hayes, D, Jr., et a . . . , Influence of Pulmonary Hypertension on Patients With Idiopathic Pulmonary Fibrosis Awaiting Lung Transplantation. Ann Thorac Surg. Jan. 2016; 101(1):246-52.
Hayes, D, Jr., et al. Pulmonary hypertension in cystic fibrosis with advanced lung disease. Am J Respir Crit Care Med. Oct. 15, 2014;190(8):898-905.
Hayes, D, Jr., et al., Prevalence of Pulmonary Hypertension and its Influence on Survival in Patients With Advanced Chronic Obstructive Pulmonary Disease Prior to Lung Transplantation. COPD. 2016;13(1):50-6.
Huang, Z. et al., Progress involving new techniques for liposome preparation. J Pharm Sci, 2014; 9(4), Aug. 2014, 176-182.
International Search Report and Written Opinion, International Patent Application No. PCT/US2018/057551, dated Jan. 7, 2019, 9 pages.
Jain, et al., Spray Drying in Pharmaceutical Industry: A Review. Research J. Pharma. Dosage Forms and Tech. 2011; 4(2): 74-79.
Kasahara, DI, et al., ROCK insufficiency attenuates ozone-induced airway hyperresponsiveness in mice. Am J Physiol Lung Cell Mol Physiol. Oct. 1, 2015;309(7):L736-46.
Lambert, JA, et al., Ozone-induced airway hyperresponsiveness: roles of ROCK isoforms. Am J Physiol Lung Cell Mol Physiol. Dec. 15, 2015;309(12):L1394-7.

(Continued)

*Primary Examiner* — Bong-Sook Baek
(74) *Attorney, Agent, or Firm* — Casimir Jones, S.C.; Tanya A. Arenson

(57) ABSTRACT

Provided herein are compositions and methods for treating pulmonary hypertension. In particular, provided herein are dry powder formulations of fasudil for delivery to the lung.

7 Claims, 29 Drawing Sheets

(56) References Cited

OTHER PUBLICATIONS

Li, X, et al., Design, characterization, and aerosol dispersion performance modeling of advanced spray-dried microparticulate/nanoparticulate mannitol powders for targeted pulmonary delivery as dry powder inhalers. J Aerosol Med Pulm Drug Deliv. Apr. 2014;27(2):81-93.

Liao, JK, et al., Rho kinase (ROCK) inhibitors. J Cardiovasc Pharmacol. Jul. 2007:50(1):17-24.

Liu. P., et al. Influence of Rho kinase inhibitor fasudil on late endothelial progenitor cells in peripheral blood of COPD patients with pulmonary artery hypertension. Bratisl Lek Listy. 2015;116(3):150-3.

Meenach, SA, et al., Characterization and aerosol dispersion performance of advanced spray-dried chemotherapeutic PEGylated phospholipid particles for dry powder inhalation delivery in lung cancer. Eur J Pharm Sci. Jul. 16, 2013;49(4):699-711.

Meenach, SA, et al., Design, physicochemical characterization, and optimization of organic solution advanced spray-dried inhalable dipalmitoylphosphatidylcholine (DPPC) and dipalmitoylphosphatidylethanolamine poly(ethylene glycol) (DPPE-PEG) microparticles and nanoparticles and nanoparticles for targeted respiratory nanomedicine delivery as dry powder inhalation aerosols. Int J Nanomedicine. 2013;8:275-93.

Meemach, SA, et al., High-performing dry powder inhalers of paclitaxel DPPC/DPPG lung surfactant-mimic multifunctional particles in lung cancer: physicochemical characterization, in vitro aerosol dispersion, and cellular studies. AAPS PharmSciTech. Dec. 2014;15(6):1574-87.

Meenach, SA, et al., Development of three-dimensional lung multicellular spheroids in air—and liquid-interface culture for the evaluation of anticancer therapeutics. Intl J Onc. Apr. 2016;48(4):1701-1709.

Muralidharan, P., et al., Microparticulate/Nanoparticulate Powders of a Novel Nrf2 Activator and an Aerosol Performance Enhancer for Pulmonary Delivery Targeting the

FIG. 21

COMPOSITIONS AND METHODS FOR DELIVERING PHARMACEUTICAL AGENTS

CROSS REFERENCE TO RELATED APPLICATION

This application is a U.S. 371 national phase entry of International Patent Application No. PCT/US2018/057551, filed Oct. 25, 2018, which claims priority to and the benefit of U.S. Provisional Application No. 62/576,957, filed Oct. 25, 2017, which are hereby incorporated by reference in their entireties.

STATEMENT REGARDING FEDERALLY SPONSORED RESEARCH OR DEVELOPMENT

This invention was made with government support under Grant Nos. R01 HL060190 and P01HL101902, awarded by NIH. The government has certain rights in the invention.

FIELD

Provided herein are compositions and methods for treating pulmonary hypertension. In particular, provided herein are dry powder formulations of fasudil for delivery to the lung.

BACKGROUND

Pulmonary hypertension (PH) is a progressive disease that leads to increased intra-arterial pressure in the pulmonary vasculature leading to heart failure. PH is categorized into several types based on its etiology (Galie N, et al., The European respiratory journal. October 2015; 46(4):903-975). The pathogenesis of PH is not well established, however, clinical manifestations include pulmonary vasoconstriction, proliferation of smooth muscle cells, migration of inflammatory cells and pulmonary vascular remodeling (Odagiri K, et al., Circulation journal: official journal of the Japanese Circulation Society. 2015; 79(6):1213-1214; Sun X Z, et al., European review for medical and pharmacological sciences. 2014; 18(7):959-964). PH can also be a serious co-morbidity that exist with other diseases such as idiopathic pulmonary fibrosis (Hayes D, Jr., et al., The Annals of thoracic surgery. January 2016; 101(1):246-252; Hayes D, Jr., Tobias J D, Mansour H M, et al. Pulmonary hypertension in cystic fibrosis with advanced lung disease. American journal of respiratory and critical care medicine. Oct. 15 2014; 190(8):898-905), chronic obstructive lung disease (COPD) (Hayes D, Jr., et al., Copd. February 2016; 13(1): 50-56). Currently, specific drug therapy for PH includes calcium channel blockers (nifedipine, diltiazem—oral administration), prostacyclin analogues and receptor agonists (beraprost—oral, epoprosteno—iv infusion, iloprost—oral, i.v, inhaled, treprostinil—i.v, subcutaneous), endothelin receptor antagonists (ambrisentan, bosentan, macitentan—oral), phosphodiesterase type 5 inhibitors and guanylate cyclase stimulators (sildenafil, tadalafil, vardenafil, riociguat—oral) or combination therapy (Galie et al., supra). However, it is also unclear if the current therapy serves to prevent the progression of the disease.

Thus, improved methods of delivering agents to the lung for treatment of PH are needed.

SUMMARY

Ease of administration with decreased off-target effects such peripheral vascular dilation is an important challenge in drug delivery in the targeted treatment of PH. This invention provides, for the first time, an advanced solid-state particle engineering design to develop dry powders for inhalation of Fas, a potent and selective RhoA kinase inhibitor, comprised of inhalable nanoparticles and microparticles. The inhalable amorphous nanoparticles and microparticles in the solid-state have properties suitable for dry powder inhalation delivery using, for example, a currently FDA-approved human DPI device. These nanoparticles find use in the treatment of a number of pulmonary diseases such as PH, asthma, and fibrosis.

Accordingly, provided herein is a composition, comprising: fasudil (Fas) nano or microparticles. In some embodiments, Fas compositions are lactose carrier-free. In some embodiments, the compositions have higher aerosol dispersion parameters than existing formulations. In some embodiments, the composition comprises amorphous particles. In some embodiments, the nano or microparticles further comprise a pharmaceutically acceptable carrier (e.g., as a molecular mixture). In some embodiments, the pharmaceutically acceptable carrier is a sugar (e.g., D-mannitol). In some embodiments, the Fas and D-mannitol are present at a molar ratio of 30:70 Fas:D-mannitol. In some embodiments, the composition is a dry powder. In some embodiments, the dry powder is spray dried. In some embodiments, the nano or microparticles have a diameter of 200 nm to 5.0 µm. In some embodiments, the nano or microparticles are generated by a method, comprising: a) preparing a first solution comprising Fas in an organic solvent; and b) spraying the first solution using a spray drying apparatus. In some embodiments, the method further comprises the steps of preparing a second solution comprising the pharmaceutically acceptable carrier in an organic solvent; and co-spraying the first and second solutions. In some embodiments, the organic solvent is methanol.

Further embodiments provide a system, comprising: a) the Fas compositions as described herein; and b) a dry powder inhaler device.

Further embodiments provide a method of treating a pulmonary disorder in a subject, comprising: administering the Fas compositions as described herein to a subject diagnosed with or having signs or symptoms of a pulmonary disorder under conditions such that said signs or symptoms are reduced. In some embodiments, the pulmonary disorder is pulmonary hypertension (PH), pulmonary fibrosis, acute lung injury (ALI), acute respiratory distress syndrome (ARDS), or asthma. In some embodiments, the method further comprises administering an additional treatment for the pulmonary disease (e.g., including but not limited to, a calcium channel blocker, a prostacyclin analogue, a prostacyclin receptor agonist, an endothelin receptor antagonist, a phosphodiesterase type 5 inhibitor, a guanylate cyclase stimulator, an inhaled or systemic corticosteroid, a bronchodilator, or a combination thereof). In some embodiments, the additional treatment is delivered in the same or different delivery device as the Fas composition. In some embodiments, the Fas composition is delivered to the lung of the subject using a dry powder inhaler device.

Further embodiments provide the use of the Fas compositions described herein to treat a pulmonary disorder in a subject diagnosed with or having signs or symptoms of a pulmonary disorder.

The Fas compositions described herein for use in treating a pulmonary disorder in a subject diagnosed with or having signs or symptoms of a pulmonary disorder.

A method of administering Fas to the lung of a subject, comprising: delivering the Fas compositions described herein to the lung of a subject using a dry powder inhaler.

Additional embodiments are described herein.

DEFINITIONS

Figure 1:
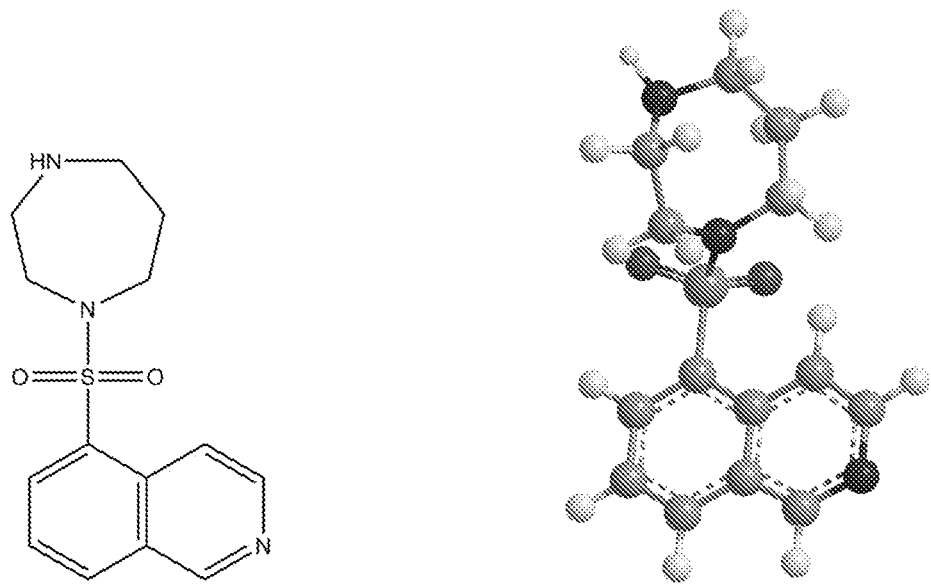
FIG. 1: Fasudil A) Chemical structure; and B) 3-D structure model.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human or non-human mammal subject.

As used herein, the term "diagnosed," as used herein, refers to the recognition of a disease by its signs and symptoms (e.g., resistance to conventional therapies), or genetic analysis, pathological analysis, histological analysis, and the like.

As used herein, the term "effective amount" refers to the amount of a compound (e.g., a compound of the present disclosure) sufficient to effect beneficial or desired results. An effective amount can be administered in one or more administrations, applications or dosages and is not limited to a particular formulation or administration route.

As used herein, the term "co-administration" refers to the administration of at least two agent(s) (e.g., a compound of the present disclosure) or therapies to a subject. In some embodiments, the co-administration of two or more agents/therapies is concurrent. In some embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, PA, (1975)).

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water and industrial samples. Such examples are not however to be construed as limiting the sample types applicable to the present disclosure.

As used herein, the terms "purified" or "to purify" refer, to the removal of undesired components from a sample. As used herein, the term "substantially purified" refers to molecules that are at least 60% free, at least 65% free, at least 70% free, at least 75% free, at least 80% free, at least 85% free, at least 90% free, at least 95% free, at least 96% free, at least 97% free, at least 98% free, at least 99% free, or 100% free from other components with which they usually associated.

As used herein, the term "modulate" refers to the activity of a compound (e.g., a compound of the present disclosure) to affect (e.g., to promote or retard) an aspect of cellular function.

As used herein, the phrase "in need thereof" means that the subject has been identified as having a need for the particular method or treatment. In some embodiments, the identification can be by any means of diagnosis. In any of the methods and treatments described herein, the subject can be in need thereof. In some embodiments, the subject is in an environment or will be traveling to an environment in which a particular disease, disorder, condition, or injury is prevalent.

DETAILED DESCRIPTION

Rho-associated protein kinase, also known as Rho-kinase or ROCK, an enzyme that belongs to the kinase family of serine-threonine kinases AGC, is a downstream effector of Rho GTPase (Amano M, et al., Cytoskeleton. September 2010; 67(9):545-554; Liao J K, et al., Journal of cardiovascular pharmacology. July 2007; 50(1):17-24). There are two isoforms, ROCK-1 and ROCK-2, which are expressed in multiple tissues, although ROCK 1 is found predominantly in liver, lung, and testis. Rho-kinase has several functions including regulation of cellular contraction, motility, morphology, polarity, cell division and gene expression (Amano M, et al., Cytoskeleton. September 2010; 67(9):545-554; Liao J K, et al., Journal of cardiovascular pharmacology. July 2007; 50(1):17-24). The Rho kinase inhibitor, fasudil competitively binds to the ATP binding site in Rho kinase and regulates the phosphorylation of myosin light chain leading to the vasodilation of constricted vessels (Sun X Z, et al., European review for medical and pharmacological sciences. 2014; 18(7):959-964). Its metabolite, hydroxyfasudil, is also active. Its effect on animal model has shown its role in vascular remodeling (Odagiri K, et al., Circulation journal: official journal of the Japanese Circulation Society. 2015; 79(6):1213-1214; Sun X Z, et al., supra). Fasudil is an approved drug in Japan for cerebral vasospasm. The Rho/ROCK signaling pathway has been implicated in many pulmonary diseases. It has been shown that decrease in pulmonary arterial pressure also decreases the progression of COPD. Liu et al. studied the effect of Fasudil on a selected number of COPD patients with PAH (Bratislayske lekarske listy. 2015; 116(3):150-153). They observed that the pulmonary artery pressure was significantly reduced in Fasudil treated patients compared to control group. An increase in the number of endothelial progenitor cells, which can play a key role in repairing damaged pulmonary arterial endothelium to reduce pulmonary artery pressure, was noted. Thus, fasudil reduced the damage and improved reconstruction of pulmonary vascular endothelium. The involvement of Rho/ROCK signaling in ozone induced airway hyper-responsiveness and inflammation has also been studied (Kasahara D I, et al., Lung cellular and molecular physiology. Oct. 1, 2015; 309(7):L736-746; Lambert J A, et al., Lung cellular and molecular physiology. Dec. 15, 2015; 309(12):L1394-1397). Fasudil has also been shown to decrease in inflammatory cells and the inflammation index in lung (Xie T, et al., Clinical and experimental allergy: journal of the British Society for Allergy and Clinical Immunology. December 2015; 45(12):1812-1822). Further, fasudil decreases allergen induced mucus hypersection by down regulating NFκB and STATE (Xie et al., supra). Rho/ROCK signaling is also involved in hypoxia induced pulmonary fibrosis and fasudil blocked the development of the fibrosis (Qi X J, et al., International journal of clinical and experimental pathology. 2015; 8(10):12140-12150). Additionally, the inhibition of Rho kinase with fasudil reduced the induction of inflammatory mediators and attenuated septic lung injury (Ding R Y, et al., The Journal of surgical research. December 2011; 171(2):e209-214). Thus, there is interest in using Fasudil, the only Rho/ROCK inhibitor currently in clinical trials, to treat PH and other diseases.

Accordingly, provided herein is a dry powder form of Fasudil (Fas) suitable for administration to the lung. In some embodiments, provided herein is a composition, comprising: fasudil (Fas) nano or microparticles. In some embodiments, the composition comprises amorphous particles. In some embodiments, the nano or microparticles have a diameter of 200 nm to 5.0 μm (e.g., 300 nm to 2 μm).

In some embodiments, Fas is present in a dry powder generated by spray drying (See e.g., below and Jain et al., Research J. Pharma. Dosage Forms and Tech. 2011; 4(2): 74-79). In some embodiments, Fas is spray dried alone or with a pharmaceutically acceptable carrier. In some embodiments, the pharmaceutically acceptable carrier is a sugar (e.g., D-mannitol, lactose, or xylitol). In some embodiments, the Fas and D-mannitol are present at a molar ratio of 75:25 to 25:75 Fas:D-mannitol.

Generally, during spray-drying, heat from a hot gas such as heated air or nitrogen is used to evaporate a solvent from droplets formed by atomizing a continuous liquid feed. If desired, the spray drying or other instruments, e.g., jet milling instrument, used to prepare the dry particles can include an inline geometric particle sizer that determines a geometric diameter of the respirable dry particles as they are being produced, and/or an inline aerodynamic particle sizer that determines the aerodynamic diameter of the respirable dry particles as they are being produced.

For spray drying, solutions, emulsions or suspensions that contain the components of the dry particles to be produced in a suitable solvent (e.g., aqueous solvent, organic solvent, aqueous-organic mixture or emulsion) are distributed to a drying vessel via an atomization device. For example, a nozzle or a rotary atomizer may be used to distribute the solution or suspension to the drying vessel. For example, a rotary atomizer having a 4- or 24-vaned wheel may be used. Examples of suitable spray dryers that can be outfitted with either a rotary atomizer or a nozzle, include, Mobile Minor Spray Dryer or the Model PSD-1, both manufactured by GEA Group (Niro, Inc.; Denmark). Actual spray drying conditions will vary depending, in part, on the composition of the spray drying solution or suspension and material flow rates. The person of ordinary skill will be able to determine appropriate conditions based on the compositions of the solution, emulsion or suspension to be spray dried, the desired particle properties and other factors. In general, the inlet temperature to the spray dryer is about 90° C. to about 300° C. The spray dryer outlet temperature will vary depending upon such factors as the feed temperature and the properties of the materials being dried. Generally, the outlet temperature is about 50° C. to about 150° C. The spray dryer outlet temperature will vary depending upon such factors as the feed temperature and the properties of the materials being dried. Generally, the outlet temperature is about 50° C. to about 150° C.

A nitrogen source with a specified moisture level may be flown over, across, or through the dry powder to add a specific moisture content to the dry powder. Such moisture can provide the desired working density of the powder. Spray drying methods in accordance with the invention are described in the Examples herein and in U.S. Pat. Nos. 6,848,197 and 8,197,845, incorporated herein by reference.

If desired, the respirable dry particles that are produced can be fractionated by volumetric size, for example, using a sieve, or fractioned by aerodynamic size, for example, using a cyclone, and/or further separated according to density using techniques known to those of skill in the art.

In some embodiments, the Fas particles are generated by a method, comprising: a) preparing a first solution comprising said Fas in an organic solvent; and b) spraying the first solution using a spray drying apparatus. In some embodiments, the method further comprises the steps of preparing a second solution comprising said pharmaceutically acceptable carrier in an organic solvent; and co-spraying the first and second solutions. In some embodiments, the organic solvent is methanol.

Administration to the respiratory tract may also be achieved by means of an aerosol formulation in which the active ingredient is provided in a pressurized pack with a suitable propellant. If the compounds or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds as an aerosol can be prepared by processes well known to the person skilled in the art. For their preparation, for example, solutions or dispersions of the compounds in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 50 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP).

The compounds may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Certain pharmaceutically acceptable salts are listed in Berge, et al., Journal of Pharmaceutical Sciences, 66:1-19 (1977), incorporated herein by reference in its entirety.

Additional embodiments provide a system, comprising: the Fas compositions described herein; and a dry powder inhaler device (e.g., commercially available devices). The inhaler may be a single dose or multi-dose inhaler.

In one aspect of this invention, an inhaler is a dry powder inhaler. A variety of inhalers can be used including the Aerolizer, Diskus, Flexhaler, Handihaler, Neohaler, Pressair, Rotahaler, Turbohaler, and Twisthaler. Other dry powder inhalers which can be used are described in U.S. Pat. Nos. 6,766,799, 7,278,425 and 8,496,002, each of which are hereby incorporated in by reference for their disclosure relating to the inhalation devices described therein. In one aspect of the invention, the compartment is a capsule or a blister pack. In one aspect of the invention, the inhaler has a resistance of about 0.05 to about 0.25, about 0.15 to about 0.25, 0.05 to about 0.15, 0.2 to about 0.25, or about 0.2. Resistance as referred herein is measured in: Square root of $CmH_2O$/Liters 20 per minute. Gravimetric analysis, using Cascade impactors, is a method of measuring the size distribution of airborne particles. Another method for measuring the size distribution of airborne particles is the Multi-stage liquid Impinger (MSLI). The MSLI is used to provide an indication of the flow rate dependence of the powder.

As used herein, the term "nominal powder dose" is the total amount of powder held in a capsule. As used herein, the term "nominal drug dose" is the total amount of Fas contained in the nominal powder dose. The nominal powder dose is related to the nominal drug dose by the load percent of drug in the powder.

Tap density can be measured by using instruments known to those skilled in the art such as the Dual Platform Microprocessor Controlled Tap Density Tester (Vankel, N.C.) or a GEOPYC™ instrument (Micrometries Instrument Corp., Norcross, GA, 30093). Tap density is a standard measure of the envelope mass density. Tap density can be determined using the method of USP Bulk Density and Tapped Density, United States Pharmacopia convention, Rockville, Md., 10th Supplement, 4950-4951, 1999. Features which can contribute to low tap density include irregular surface texture and porous structure. The envelope mass density of an isotropic particle is defined as the mass of the particle divided by the minimum sphere envelope volume within which it can be enclosed.

The diameter of the spray-dried particles, for example, the VMGD, can be measured using a laser diffraction instrument (for example Helos, manufactured by Sympatec, Princeton, N.J.). Other instruments for measuring particle diameter are well known in the art.

In some embodiments, the inhalable powder comprising Fas as described above is used to fill capsules suitable for use in an inhaler. The term "capsule material" as used herein refers to the material from which the shell of the capsule for inhalation is made. In one embodiment, the capsule material according to the invention is selected from among gelatin, cellulose derivatives, starch, starch derivatives, chitosan and synthetic plastics. If gelatin is used as the capsule material, examples according to the invention may be selected from among polyethyleneglycol (PEG), PEG 3350, glycerol, sorbitol, propyleneglycol, PEO-PPO block copolymers and other polyalcohols and polyethers. If cellulose derivatives are used as the capsule material, examples according to the invention may be selected from hydroxypropylmethylcellulose (HPMC), hydroxypropylcellulose, methylcellulose, hydroxymethylcellulose and hydroxyethylcellulose. If synthetic plastics are used as the capsule material, examples according to the invention may be selected from polyethylene, polycarbonate, polyester, polypropylene and polyethylene terephthalate. In one embodiment, the capsule material further comprises titanium dioxide. In one preferred embodiment the capsule comprises HPMC and titanium dioxide. In one embodiment, the capsule comprises carrageenan. In a further embodiment, the capsule comprises potassium chloride. In a still further embodiment, the capsule comprises, HPMC, carrageenan, potassium chloride, and titanium dioxide. In one embodiment, the capsule size is selected from 000, 00, 0, 1, or 2.

In one aspect of the invention, the powders have low electrostatic charge to enable high dispersion from the capsule. The capsules of the invention are particularly suitable for use in a dry powder inhaler for the delivery of a dry powder composition comprising an effective amount of Fas to a patient in need thereof for example, for treating pulmonary disease.

The present invention provided methods of administering Fas to the lung for any use (e.g., treatment of diseases currently treated with Fas such as PH, pulmonary fibrosis, acute lung injury (ALI), acute respiratory distress syndrome (ARDS), or asthma or other disorders not currently treated by Fas.

Further embodiments provide a method of treating pulmonary disease (e.g., PH, pulmonary fibrosis, or asthma) in a subject, comprising: administering the Fas compositions described herein to a subject diagnosed with or having signs or symptoms of pulmonary disease under conditions such that the signs or symptoms are reduced. In some embodiments, the method further comprises administering an additional treatment for pulmonary disease (e.g., including but not limited to, a calcium channel blocker, a prostacyclin analogue, a prostacyclin receptor agonist, an endothelin receptor antagonist, a phosphodiesterase type 5 inhibitor, a guanylate cyclase stimulator, an inhaled or systemic corticosteroid, a bronchodilator, or a combination thereof). In some embodiments, the composition s administered to the lung of the subject using a dry powder inhaler.

EXPERIMENTAL

Example 1

Experimental: Materials and Methods
Materials
Fasudil monohydrochloride hemihydrate salt (Fas) [$C_{14}H_{17}N_3O_2S$; molecular weight (MW): 291.36 g/mol], shown in FIG. 1 (ChemDraw Ultra Ver. 10.0.; CambridgeSoft, Cambridge, Mass.), was obtained from LC laboratories (Woburn, MA, USA). Methanol (HPLC grade, ACS-certified grade, purity 99.9%) was obtained from Fisher Scientific (Fair Lawn, New Jersey). HYDRANAL®-Coulomat AD was obtained from Sigma-Aldrich. The nitrogen gas used was ultra-high purity (UHP) nitrogen gas (Cryogenics and gas facility, The University of Arizona, Tucson, Arizona). Raw Fas was stored in sealed glass desiccators over Indicating Drierite/Drierite™ desiccant at temperature below −20° C. D-Man was used as received and stored under room conditions. Other chemicals were stored under room conditions.

Methods
Preparation of Spray Dried particles by Organic Solution Advanced Spray Drying in Closed Mode Organic solution advanced spray drying process in the absence of water was performed in closed mode using a Büchi B-290 Mini Spray Dryer with a high performance cyclone in closed mode using UHP dry nitrogen gas as the atomizing drying gas and connected to the B-295 Inert Loop (Buchi Labortechnik AG, Flawil, Switzerland). The feed solution was prepared by dissolving 0.5% w/v of the drug in methanol using Branson 7500 ultrasonicator to aid in dissolution. Table 1 lists the spray drying conditions for Fas powders. The drying gas atomization rate (670 L/h at 35 mmHg) and aspiration rate (35 m3/h at 100% rate) was maintained constant during all the experiments. Four feed input rates were employed to obtained particles using pump rates of 7.5 mL/min (25%), 15 mL/min (50%), 22.5 mL/min (75%) and 30 mL/min (100%). The stainless steel two-fluid nozzle tip diameter was 0.7 mm with 1.5 mm gas cap. The SD particles were separated from the nitrogen drying gas in the high-performance cyclone (HPC) and collected in the small sample collector. All spray dried (SD) powders were carefully stored in sealed glass vials stored in sealed glass desiccators over indicating Drierite/Drierite™ desiccant at −20.0 under ambient pressure.

Scanning Electron Microscopy (SEM) and Energy Dispersive X-Ray (EDX) Spectrometry Using conditions similar to those previously reported (Li X, et al., Journal of aerosol medicine and pulmonary drug delivery. April 2014; 27(2):81-93; Meenach S A, et al., European journal of pharmaceutical sciences: official journal of the European Federation for Pharmaceutical Sciences. Jul. 16, 2013; 49(4):699-711; Meenach S A, et al., International journal of nanomedicine. 2013; 8:275-293), visual imaging and analysis of particle size, morphology, and surface morphology was achieved by scanning electron microscopy (SEM). The powder samples were placed on double coated carbon conductive adhesive Pelco tabs' (TedPella, Inc. Redding CA), which were adhered to aluminum stubs (Ted-Pella, Inc.) Subsequently, the powder sample in the stub was sputter coated with thin film of gold using Anatech Hummer 6.2 (Union city, CA, USA) system at 20 µA for 90 secs under Argon plasma. The electron beam with an accelerating voltage of 30 kV was used at a working distance of 10-10.4 mm. SEM images were captured by SEM FEI Inspect S (Brno, Czech Republic) at several magnification levels. EDX was performed using ThermoNoran systems Six (Thermo Scientific, Waltham, Mass., USA) at accumulation voltage of 30,000 eV, the spot size was increased until a dead time of 20-30 was obtained.

Particle Sizing and Size Distribution Using SEM Micrographs

The mean size, standard deviation and size range of the particles were determined digitally using Sigma Scan Pro 5.0.0 (Systat, San Jose, CA, USA), using similar conditions that have been previously reported (Meenach S A, et al., AAPS PharmSciTech. December 2014; 15(6):1574-1587; Duan J, et al., International journal of nanomedicine. 2013; 8:3489-3505). Representative micrographs for each particle sample at 15,000× magnification was analyzed by measuring the diameter of at least 100 particles per sample.

X-Ray Powder Diffraction (XRPD)

Using conditions similar to those previously reported (Li et al., 2014, supra; Meenach S A, et al., European journal of pharmaceutical sciences: official journal of the European Federation for Pharmaceutical Sciences. Jul. 16, 2013; 49(4):699-711; Meenach S A, et al., International journal of nanomedicine. 2013; 8:275-293), X-ray powder diffraction (XRPD) patterns of samples were collected at room temperature with a PanAnalytical X'pert diffractometer (PANalytical Inc., Westborough, Mass., USA) with Cu Kα radiation (45 kV, 40 mA, and λ=1.5406 A°) between 5.0° and 50.0° (2θ) with a scan rate of 2.00°/minute at ambient temperature. The powder samples were either directly loaded on zero background silicon wafer sample holder or were filled into glass capillary that was placed on the silicon wafer sample holder and the diffraction was measured with an X'celerator detector.

Differential Scanning Calorimetry (DSC)

Using conditions similar to those previously reported (Li et al., 2014, supra; Meenach S A, et al., European journal of pharmaceutical sciences: official journal of the European Federation for Pharmaceutical Sciences. Jul. 16, 2013; 49(4):699-711; Meenach S A, et al., International journal of nanomedicine. 2013; 8:275-293), thermal analysis and phase transition measurements were performed on a TA Q1000 differential scanning calorimeter (DSC) (TA Instruments, New Castle, Del.) equipped with T-Zero® technology, RSC90 automated cooling system, auto sampler and calibrated with indium. Approximately 1-10 mg sample was placed into an anodized aluminum hermetic DSC pan. The T-Zero® DSC pans were hermetically sealed with the T-Zero hermetic press (TA Instruments). An empty hermetically sealed aluminum pan was used as reference pan for all the experiments. UHP nitrogen was used as the purging gas at a rate of 40 mL/min. The samples were heated from 0.00° C. to 250.00° C. at a scanning rate of 5.00° C./min. All measurements were carried out in triplicate (n=3).

Hot Stage Microscopy (HSM) Under Cross-Polarizers

Using conditions similar to those previously reported (Li et al., 2014, supra; Meenach S A, et al., European journal of pharmaceutical sciences: official journal of the European Federation for Pharmaceutical Sciences. Jul. 16, 2013; 49(4):699-711; Meenach S A, et al., International journal of nanomedicine. 2013; 8:275-293), hot-stage microscopy (HSM) studies used a Leica DMLP cross-polarized microscope (Wetzlar, Germany) equipped with a Mettler FP 80 central processor heating unit and Mettler FP82 hot stage (Columbus, OH, USA). Samples were mounted on glass slide and heated from 25.0° C. to 250.0° C. at a heating rate of 5.00° C./min. The images were digitally captured using a Nikon coolpix 8800 digital camera (Nikon, Tokyo, Japan) under 10× optical objective and 10× digital zoom.

Karl Fisher Titration (KFT)

Using conditions similar to those previously reported (Li et al., 2014, supra; Meenach S A, et al., European journal of pharmaceutical sciences: official journal of the European Federation for Pharmaceutical Sciences. Jul. 16, 2013; 49(4):699-711; Meenach S A, et al., International journal of nanomedicine. 2013; 8:275-293), the residual water content of all SD powders were quantified analytically by Karl Fischer titration (KFT) coulometrically using a TitroLine 7500 trace titrator (SI Analytics, Germany). Approximately 2-10 mg of powder was added to the titration cell containing Hydranal® Coulomat AD reagent. The residual water content was measured at the end of titration.

Confocal Raman Microspectroscopy (CRM), Chemical Imaging, and Mapping

Confocal Raman microspectroscopy (CRM) provides noninvasive and nondestructive microspectroscopic component analysis of DPI formulations. Using conditions similar to those previously reported (Li et al., 2014, supra; Meenach S A, et al., European journal of pharmaceutical sciences: official journal of the European Federation for Pharmaceutical Sciences. Jul. 16, 2013; 49(4):699-711; Meenach S A, et al., International journal of nanomedicine. 2013; 8:275-293), Raman spectra was obtained at 514 nm and 785 nm laser excitations using Renishaw InVia Reflex (Gloucestershire, UK) at the surface using a 20× magnification objective on a Leica DM2700 optical microscope (Wetzlar, Germany) and equipped with a Renishaw inVia Raman system (Gloucestershire, UK). This Renishaw system has a 2400 Umm grating, with a slit width of 65 µm and a thermoelectrically cooled Master Renishaw CCD detector. The laser power was adjusted to achieve 5000 counts per second for the 520 $cm^{-1}$ line of the internal Si Reference. All spectra were subjected to baseline correction prior to further analysis.

Attenuated Total Reflectance—FTIR Spectroscopy

A Nicolet 6700 FTIR spectrometer (Thermo electron corporation, Madison, WI, USA) fitted with smart performer (Thermo scientific, Waltham, MA, USA) attenuated total reflectance (ATR) accessory was used for all the experiments. Each spectrum was collected for 32 scans at a spectral resolution of 8 $cm^{-1}$ over the wavenumber range of 4000-400 $cm^{-1}$. A background spectrum was carried out under the same experimental conditions and was subtracted from each sample spectrum. Spectral data were acquired with EZ-OMNIC software. These conditions are similar to previous studies (Li et al., 2014, supra; Meenach S A, et al., European journal of pharmaceutical sciences: official journal of the European Federation for Pharmaceutical Sciences. Jul. 16, 2013; 49(4):699-711; Meenach S A, et al., International journal of nanomedicine. 2013; 8:275-293).

In Vitro Aerosol Dispersion Performance

In accordance with USP Chapter <601> specifications (Aerosols, Nasal Sprays, Metered-Dose Inhalers, and Dry Powder Inhalers Monograph. USP 29-NF 24. The United States Pharmacopoeia and The National Formulary: The Official Compendia of Standards. Vol 29/24. Rockville, MD: The United States Pharmacopeial Convention, Inc.; 2006: 2617-2636) on aerosols and using conditions similar to those previously reported (Li et al., 2014, supra; Meenach S A, et al., European journal of pharmaceutical sciences: official journal of the European Federation for Pharmaceutical Sciences. Jul. 16, 2013; 49(4):699-711; Meenach S A, et al., International journal of nanomedicine. 2013; 8:275-293), the aerosol dispersion performance of SD Fas particles was tested using the Next Generation Impactor™ (NGI™) (MSP Corporation, Shoreview, Minnesota, USA) with a stainless steel induction port (USP throat) attachment (NGI Model 170; MSP Corporation) equipped with specialized stainless steel NGI gravimetric insert cups (MSP Corporation). Three FDA-approved human DPI devices Aerolizer® (Merck), Neohaler® (Sunovion Pharmaceuticals) and HandiHaler® (Boehringer Ingelheim) were used for aerosol dispersion. An airflow rate (Q) of 60 L/min (DPI airflow rate) was adjusted and measured before each experiment using a COPLEY DFM 2000 flow meter (COPLEY Scientific, Nottingham, United Kingdom). The NGI was connected to a COPLEY HCPS vacuum pump (COPLEY Scientific) through a COPLEY TPK 2000 critical flow controller (COPLEY Scientific). The mass of powder deposited on each stage was quantified by gravimetric method using type A/E glass fiber filters with diameter 55 mm (PALL Corporation, Port Wash., N.Y.) and 75 mm (Advantec, Japan). Quali-V-I clear HPMC size 3 inhalation grade capsules (Qualicaps, North Carolina) were filled with about 10 mg of powder. Three capsules were used in each experiment. In vitro aerosolization was evaluated (n=3) under ambient conditions.

For the NGI, Q=60 L/min, the $D_a50$ aerodynamic cutoff diameter for each NGI stage was calibrated by the manufacturer and stated as: stage 1 (8.06 μm); stage 2 (4.46 μm); stage 3 (2.82 μm); stage 4 (1.66 μm); stage 5 (0.94 μm); stage 6 (0.55 μm); and stage 7 (0.34 μm). The emitted dose (ED) was determined as the difference between the initial mass of powder loaded in the capsules and the remaining mass of powder in the capsules following aerosolization. The ED (%) Equation 1 was used to express the percentage of ED based on the total dose (TD) used. The fine particle dose (FPD) was defined as the dose deposited on stages 2 to 7. The fine particle fraction (FPF %) Equation 2 was expressed as the percentage of FPD to ED. The respirable fraction (RF %) Equation 3 was used as the percentage of FPD to total deposited dose (DD) on all impactor stages.

$$\text{Emitted Dose fraction } (ED\ \%) = \frac{ED}{TD} \times 100\% \quad \text{Equation 1}$$

$$\text{Fine Particle Fraction } (FPF\ \%) = \frac{FPD}{ED} \times 100\% \quad \text{Equation 2}$$

$$\text{Respirable Fraction } (RF\ \%) = \frac{FPD}{DD} \times 100\% \quad \text{Equation 3}$$

In Vitro Drug Dose-Response Cell Viability

Cell-based assays are often used to determine if test molecules have effects on cell proliferation or show direct cytotoxicity effects that eventually leads to cell death. The effects of the drug formulations were analyzed by measuring the response of lung adenocarcinoma cells at different concentrations of the drug. The A549 pulmonary cell line is a human alveolar epithelial lung adenocarcinoma cell line and has been used as a model of the alveolar type II pneumocyte cell in in vitro pulmonary drug delivery and metabolism studies. The H348 pulmonary cell line is a human bronchoalveolar epithelial cell line similar to alveolar type II cells and express lung surfactant associated protein A (SP-A) (Acosta M F, et al., Current pharmaceutical design. 2016; 22(17):2522-2531). Both cell lines were grown in a growth medium including Dulbecco's modified Eagle's medium (DNEM) advanced 1×, 10% (v/v) fetal bovine serum (FBS), Pen-Strep (100 U ml$^{-1}$ penicillin, 100 μg ml$^{-1}$), Fungizone (0.5 μg ml$^{-1}$ amphotericin B, 0.41 μg ml$^{-1}$ sodium deoxycholate), and 2 mM L-Glutamine in a humidified incubator at 37° C. and 5% $CO_2$. As previously reported (Acosta et al., 2016, supra), both cell lines were seeded in 96-well plates at 5000 cells/well and 100 μl/well and allowed to attach for 48 hours. Then, the cells were exposed to 100 μl of Fas dissolved in media at different concentrations and incubated for 72 hours after exposure. 20 μl of 10 μM resazurin sodium salt dissolved in 1% DMSO in media was added to each well and incubated for 4 hours. At this point, the fluorescence intensity was detected at 544 nm (excitation) and 590 nm (emission) using a Synergy H1 Multi-Mode Reader (BioTek Instruments Inc., Winooski, Vt.). The relative viability of each sample was calculated as follow:

$$\text{Relative viability } (\%) = \frac{\text{Sample fluorescence intensity}}{\text{Control fluorescence intensity}} \times 100\% \quad \text{Equation 4}$$

In Vitro Transepithelial Electrical Resistance Analysis

Calu-3 lung epithelial cells, a human lung adenocarcinoma cell line derived from the bronchial submucosal airway region, were grown in a growth medium including Eagle's minimum essential medium (EMEM), 10% (v/v) fetal bovine serum (FBS), Pen-Strep (100 U ml-1 penicillin, 100 μg ml-1), Fungizone (0.5 μg ml-1 amphotericin B, 0.41 μg ml-1 sodium deoxycholate) in humidified incubator at 37° C. and 5% $CO_2$, as previously reported (Acosta et al., 2016, supra; Acosta M F, et al., 2016, supra). The cells were seeded at 500,000 cells/ml in Costar Transwells® (0.4 μm polyester membrane, 12 mm for a 12-well plate) with 0.5 ml of media on the apical side and 1.5 ml of media on the basolateral side. Media was changed every other day from the basolateral and apical side. After 10 days of growth, when the cells reached a TEER value of about 1000 Ω/cm$^2$ which is an indicator of a confluent monolayer at liquid covered culture (LCC), the media was removed from both sides and 800 μl of media was added to the basolateral side of the Transwells to facilitate air-interface culture (AIC) conditions. The TEER responses of the cells were measured with an Endohom 12 mm Culture Cup (World Precision Instruments, Sarasota, FL). For TEER measurement, 0.5 ml of media was added to the apical side of the Transwell 5 min before measurement and then immediately removed to return the cells to AIC conditions. After the TEER values reached 500 Ω/cm$^2$ which is an indication of a confluent monolayer at AIC conditions, the cells were exposed to 100 μM of representative formulations dissolved in non-supplemented EMEM media. The liquid aerosol formulations were delivered to the Calu-3 cells at AIC by using a Penn Century MicroSprayer® Aerolizer—Model IA-1B [1]. TEER values were then recorded for up to 7 days after aerosol treatment, as previously reported (Meenach S A, et al., AAPS PharmSciTech. 2014; 15(6):1574-1587; Meenach S A, et al., April 2016; 48(4):1701-1709).

Statistical Analysis

The Design of experiments (DoEs) for in vitro aerosol performance was conducted using Design Expert® 8.0.7.1 software (Stat Ease Corporation, Minneapolis, Minnesota). A full factorial multi-level design was used for in vitro aerosol performance experiment randomization and post-run analysis. Interaction of process parameter on the performance of the SD formulations was evaluated with analysis power of 99.1 and 93 for device resistance and pump rate using Design Expert®. All experiments were performed in triplicate (n=3) unless otherwise mentioned. Results are expressed as mean±standard deviation.

Results

SEM—EDX

Figure 2:
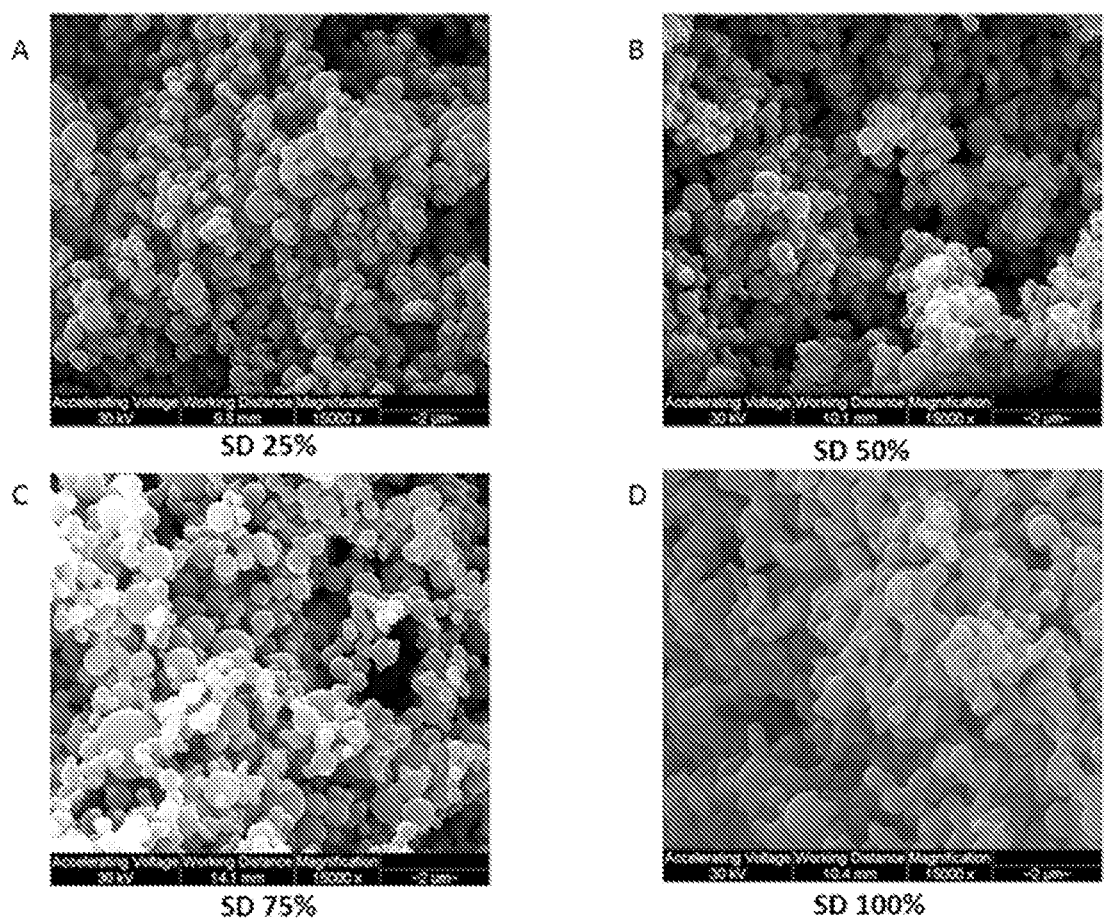
FIG. 2: SEM micrographs of SD Fas at 15,000× A) SD 25% PR; B) SD 50% PR; C) SD 75% PR; and D) SD 100% PR.

At all pump rates, SEM micrographs of SD Fas alone revealed small, spherical particles. The morphology of all SD Fas particles was found to be smooth, as shown in FIG. 2. A pump rate effect was noticed such that as the pump rate increased from 25% to 100% the shape of the particles became less spherical. At higher pump rates of 75% and 100%, solid sintering between the spray dried particles were observed.

Figure 3:
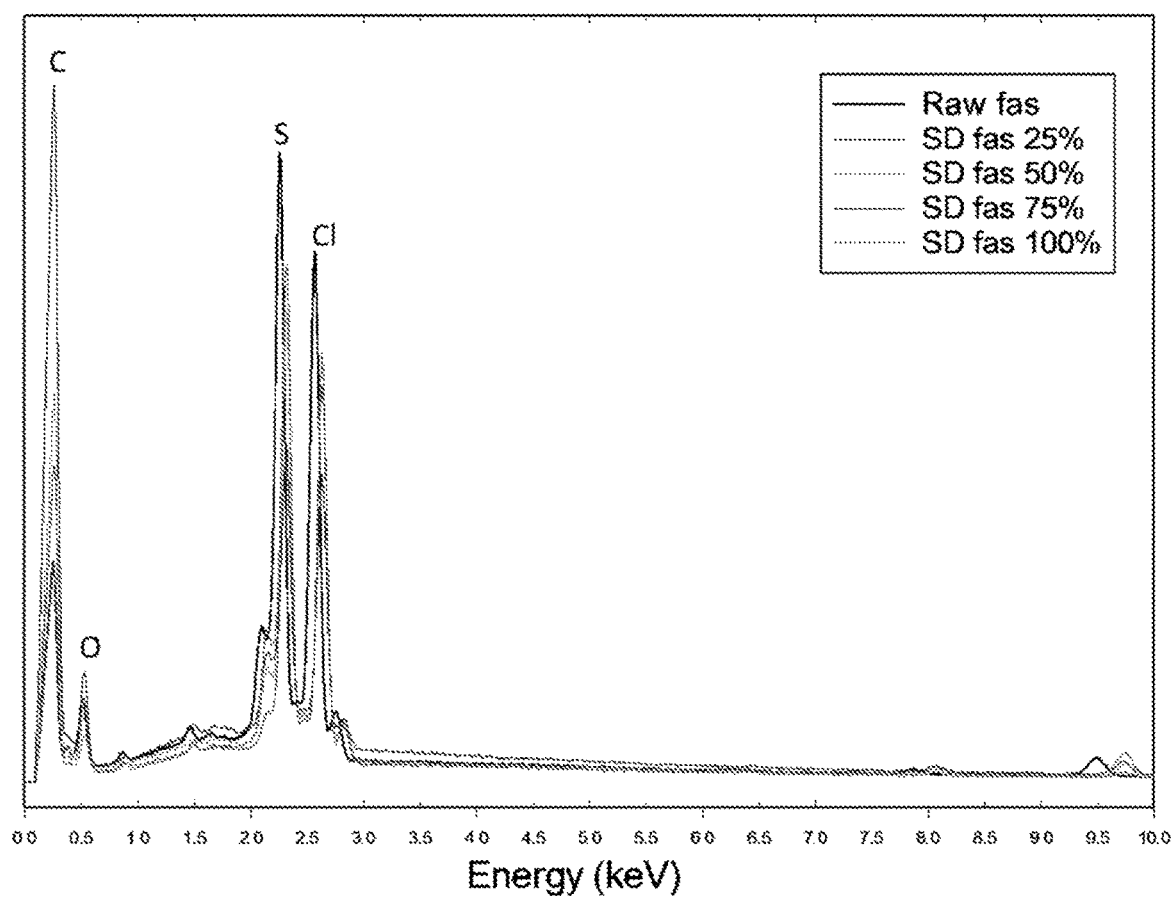
FIG. 3: EDX spectra of A) raw and SD Fas showing characteristic peaks. C—Carbon, O—Oxygen, S—sulfur and Cl—chlorine atoms.

The energy dispersive X-ray (EDX) spectra of the powders are shown in FIG. 3. For chemical identification of Fas, the characteristic Kα line (peaks) of Sulphur (S) is seen at 2.3 keV and the Kα line of chlorine (Cl) is seen at 2.63 keV. The Kα lines of carbon (C) at 0.257 keV and oxygen (O) at 0.526 keV obscure the peaks of nitrogen (N) which is usually seen at 0.392 keV. The peaks corresponding to S and Cl are representative of Fas. All SD (FIG. 3) Fas powders possess these peaks in their EDX spectrum, indicating the presence of Fas as an acid salt before and after spray drying.

Particle Sizing and Size Distribution Using SEM Micrographs

Table 2 lists the particle size range, mean particle size and standard deviation of the SD Fas particles sized from SEM micrographs using Sigma Scan Pro software. As can be seen from Table 2, SD Fas alone formed particles in the nanometer range. Specifically, 25% pump rate formed particles in the range of 270 nm-1.67 μm, 50% pump rate formed 343 nm-1.94 μm, 75% pump rate formed 346 nm-3.20 μm and 100% pump rate formed 454 nm-2.78 μm.

X-Ray Powder Diffraction (XRPD)

Figure 4:
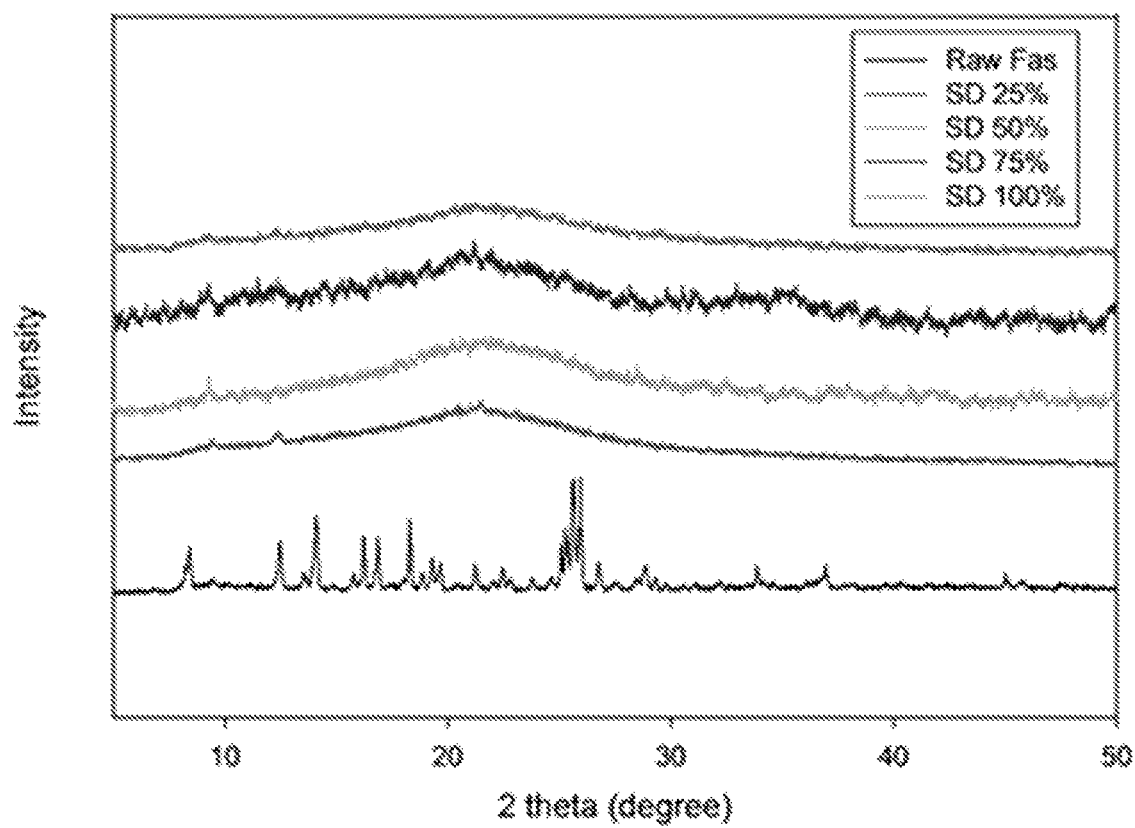
FIG. 4: XRPD diffraction patterns of Raw and SD Fas powders at different spray drying pump rates.

Raw Fas had rich and intense X-ray diffraction peaks from about 8°-28° 2θ. The characteristic peaks and other diffraction peaks seen including 8.4°, 14.1°, 16.2°, 16.8°, 18.3°, 19.6°, 21.2°, 22.4°, 25.6° and 25.9° 2θ degree are similar to previously reported X-ray diffraction of Fasusil hemihydrate (Ohno H K M, Inventor; Asahi Kasei Kogyo Kabushiki Kaisha, Osaka, Japan, assignee. 1-(5-isoquinolinesulfonyl) homopiperazine hydrochloride hydrates. U.S. Pat. No. 5,942,505. Aug. 24, 1999, 1997). The several diffraction peaks of raw Fas in FIG. 4 are indicative of the presence of long-range molecular order in the raw sample. On the other hand, SD fas particles at all pump rates exhibited no diffraction peak (FIG. 4), unlike the raw sample, which is interpreted as the lack of long-range molecular order in SD Fas particles.

Differential Scanning Calorimetry (DSC)

Figure 5:
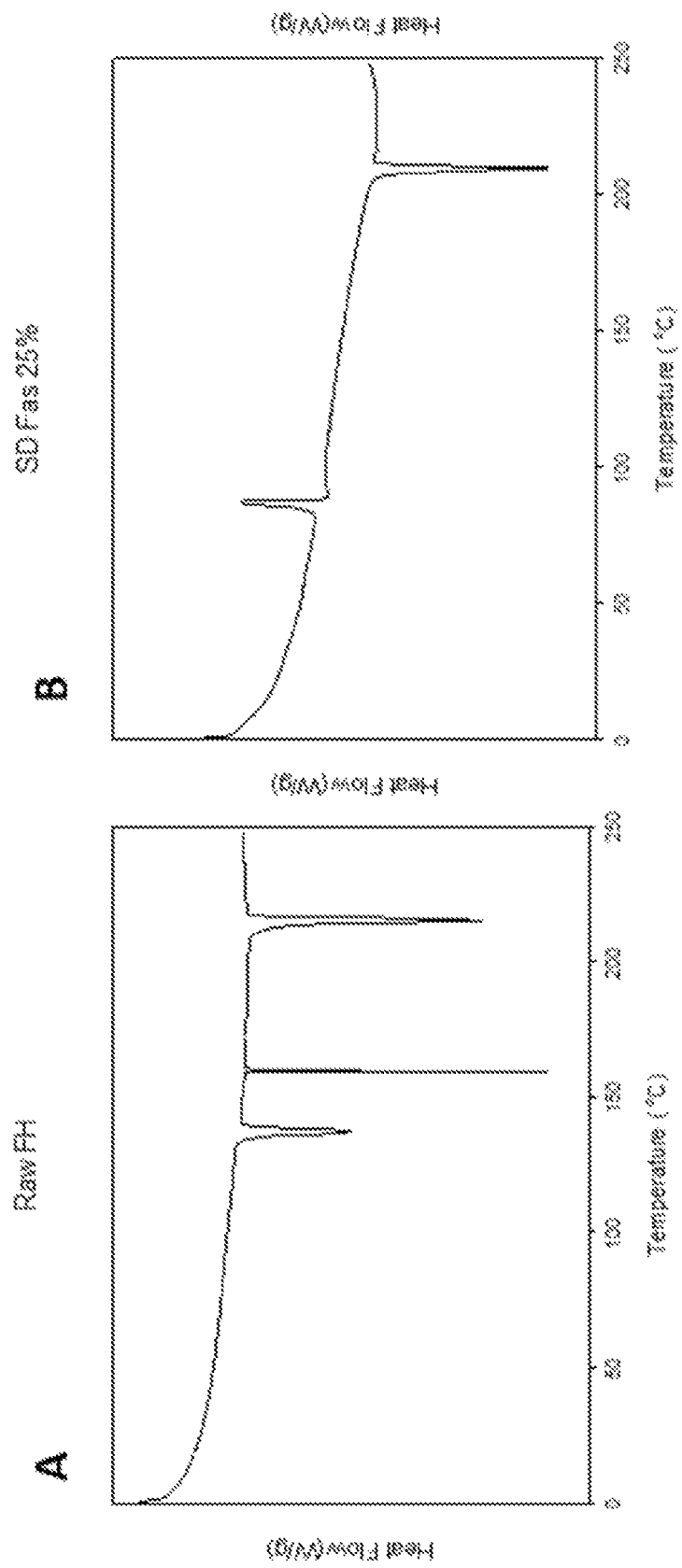
FIG. 5: DSC thermograms of raw and SD fas A) Raw Fas; B) SD fas 25% pump rate; C) SD fas 50% pump rate; D) SD fas 75% pump rate; and E) SD Fas 100% pump rate.
Figure 5:
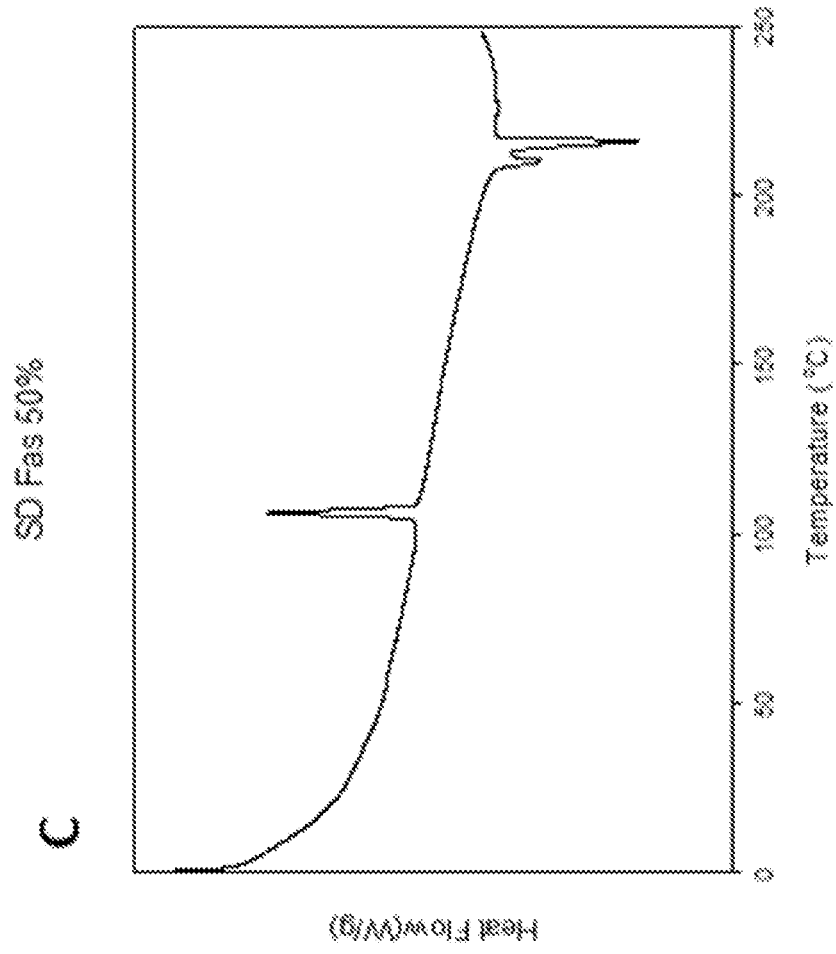
Figure 5:
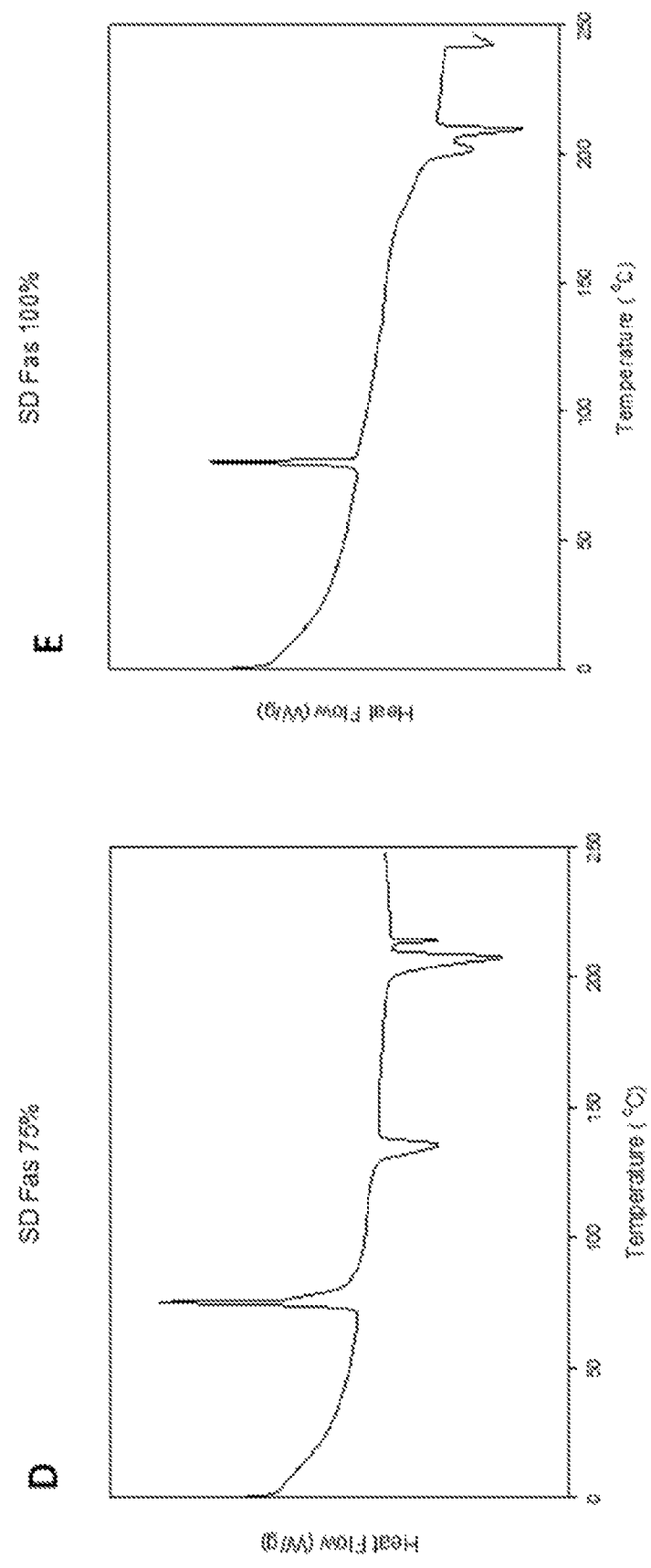

As shown in FIG. 5, raw Fas exhibited three endothermic transitions at 137°, 160° and 215° C. with no signs of amorphous character. The melting at 137° C. is dehydration of the hemihydrate followed by melting of the anhydrous form. On spray drying, all particles showed only endothermic transitions. The glass transition (Tg) temperature of SD fas was evident and was found to be between 47°-52° C. The single component SD fas particles at all pump rates also possessed an exotherm between 75°-108° C. indicating a phase transition from disordered to ordered phase at this temperature range. However, 25% PR exhibited a single endotherm around 209° C. after the transition, while other pump rates exhibited, at least, two endotherms. The exact transition temperatures are listed in Table 3. The predicted melting point of Fas is around 220° C.

Hot Stage Microscopy (HSM) Under Cross-Polarizers

Figure 6:
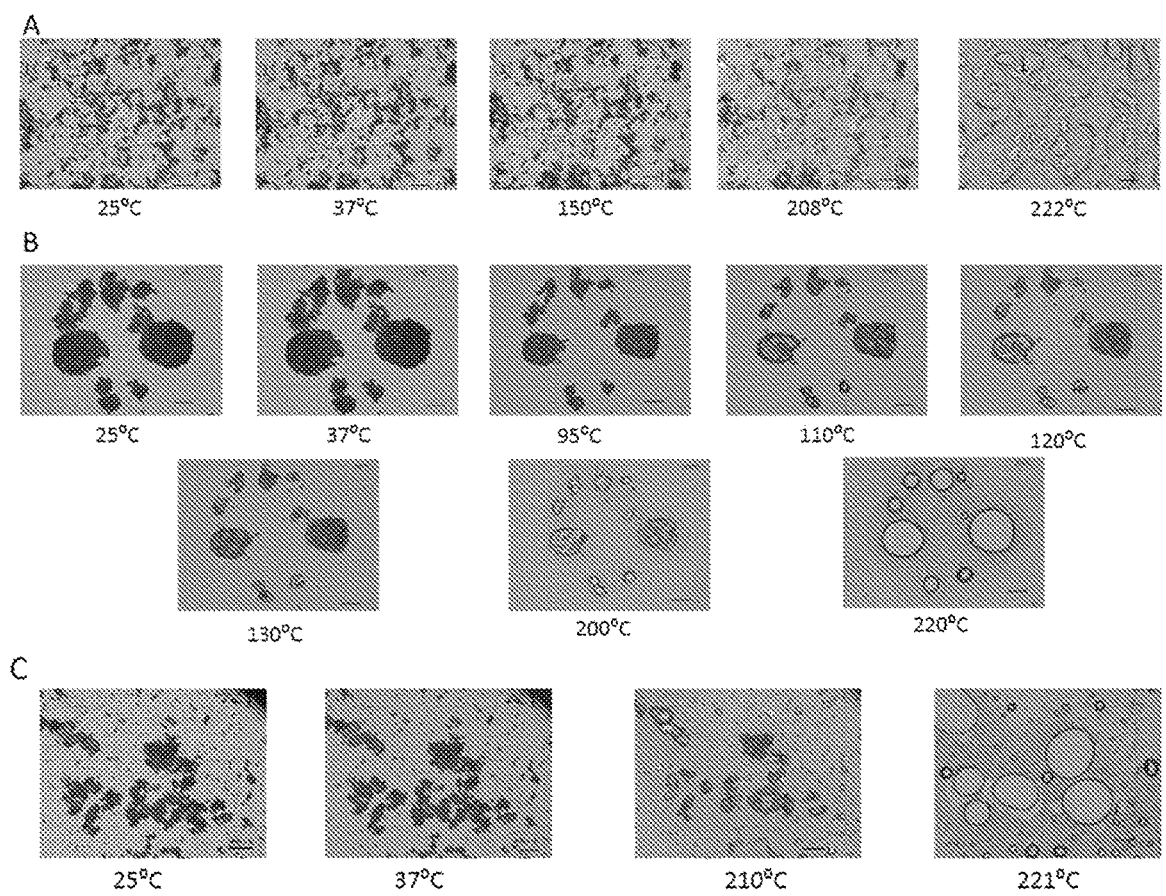
FIG. 6: Representative HSM images of A) Raw Fas; B) SD fas 25% pump rate; and C) SD Fas 100% pump rate.
Figure 7:
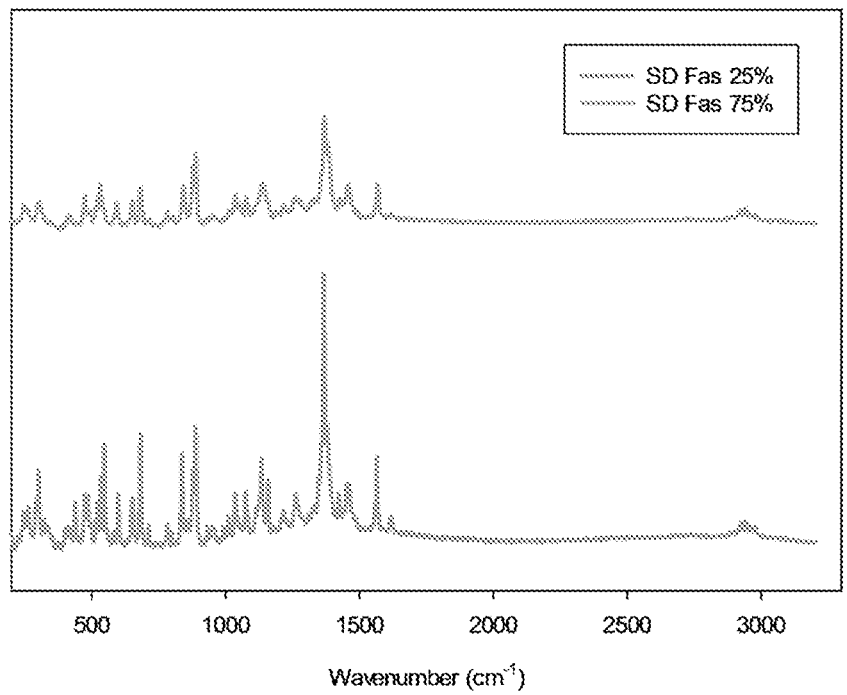
FIG. 7: Representative Raman spectra of selected SD Fas formulations obtained using 785 nm laser.
Figure 8:
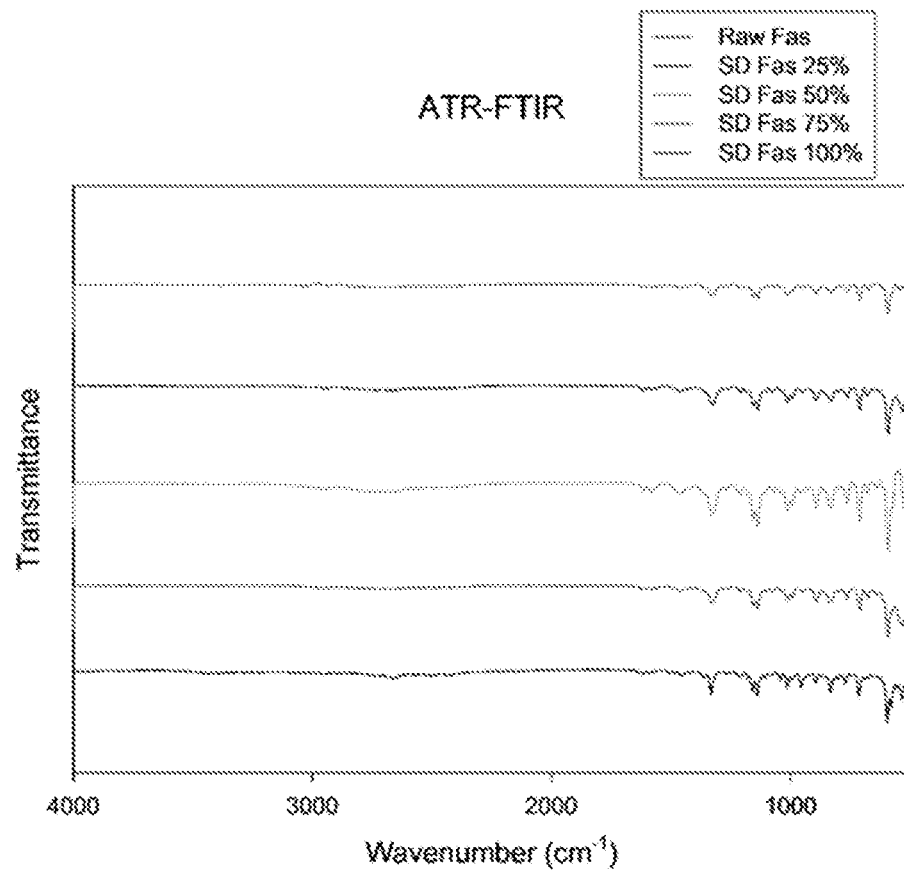
FIG. 8: ATR-FTIR spectrum of Raw and SD Fas at different spray drying conditions.

As visualized by cross polarized light microscopy, raw Fas exhibits no change in birefringence until 150° C., where there was a change in birefringence followed by the start of melting at 208° C. with a cloudy appearance as shown in FIG. 6. The particles possessed birefringence while melting and the melting completed at around 222° C. SD fas (25%) birefringence remained unchanged until 95° C. (FIG. 6). After that a change in particle size similar to particle shrinkage was seen followed by the appearance of birefringence around 110° C., then change in birefringence between 120° and 130° C. and finally melting from 200° C. to 220° C. Similarly, SD fas at 50% and 75% pump rate showed particle shrinkage and several changes in birefringence after 93° C. and 43° C. respectively before they melted around 220-223° C. SD Fas at 100% showed no changes in birefringence until 210° C., where melting started and ended at 221° C.

Karl Fisher Titration (KFT)

The measured residual water content of raw, SD Fas powders are tabulated in Table 4. As seen from the table, raw Fas had a water content of 2.97% w/w, while SD Fas particles had residual water in the range of 2.45-3.22% w/w.

Confocal Raman Microspectroscopy (CRM) and Chemical Imaging

Initially, Raman spectral scanning was performed using various laser power. The powder sample exhibited an enormous amount of fluorescence, where the Raman peaks were obscured by fluorescence of the samples. Hence, 785 nm laser was used to obtain the Raman signals of selected formulations. Raman peaks of Raw Fas were seen at 112, 841, 1366, 1382 and 1566 Raman shift/cm$^{-1}$. The Raman peaks seen in FIG. 5.7 were obtained using 785 nm laser, representative SD fas powder shows that the Raman shift didn't change after spray drying.

Attenuated Total Reflectance—FTIR Spectroscopy

Assigning groups to every peak in IR spectrum is difficult since there are many overlaps in bands. However, some characteristic peaks of Fas were identified in the ATR-FTIR spectrum in FIG. 5.8 at approximately 1159 cm$^{-1}$ ($SO_2$ symmetric stretching) low energy for symmetric stretch and slightly more energy for an anti-symmetric stretch at 1332 cm$^{-1}$ ($SO_2$ antisymmetric stretch) characteristics of sulfonamide group. The slight peak seen around 1620 cm$^{-1}$ (stretching of aromatic ring) is indicative of isoquinoline. These are similar to previous reports of Fas hemihydrate (Ohno H K M, Inventor; Asahi Kasei Kogyo Kabushiki Kaisha, Osaka, Japan, assignee. 1-(5-isoquinolinesulfonyl) homopiperazine hydrochloride hydrates. U.S. Pat. No. 5,942,505. Aug. 24, 1999, 1997). The spectral pattern seen at fingerprint region (<1500 wavenumber) was consistently observed in all SD and raw Fas samples where the peaks were found at approximately 710, 836, 892, 1012, 1136 and 1325 cm$^{-1}$.

In Vitro Aerosol Dispersion Performance

Figure 9A:
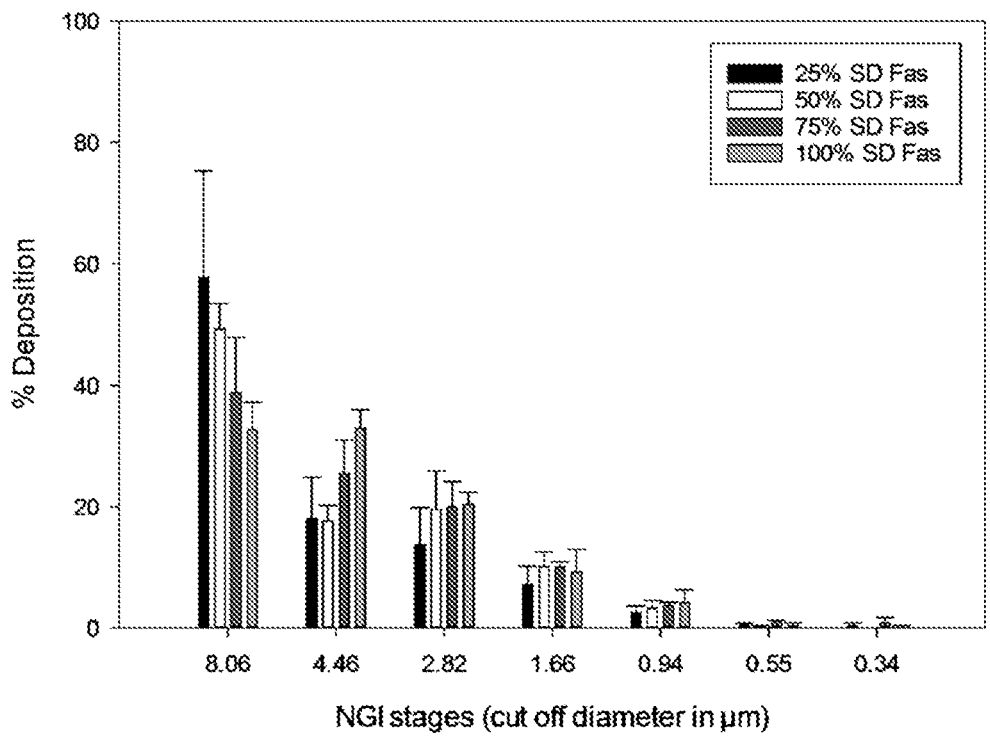
FIG. 9: In vitro aerosol dispersion performance of SD Fas powders at all pump rates using the NGI and the FDA-approved human DPI devices; A) Aerolizer®, B) Neohaler®, and C) Handihaler®.
Figure 9B:
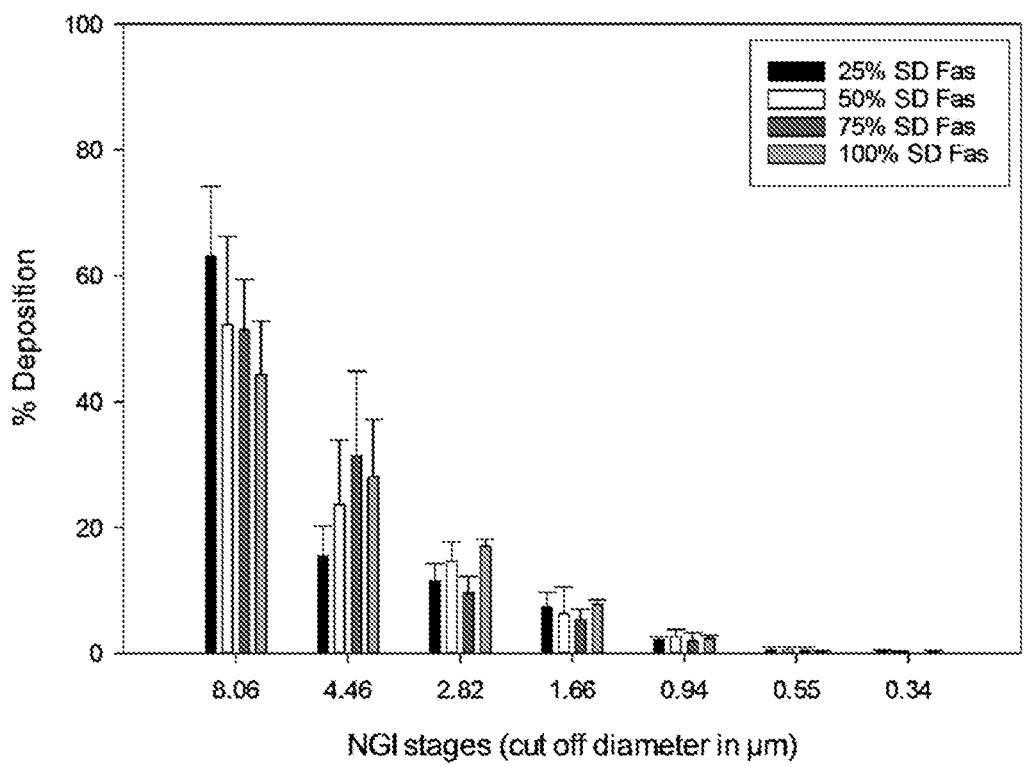
Figure 9C:
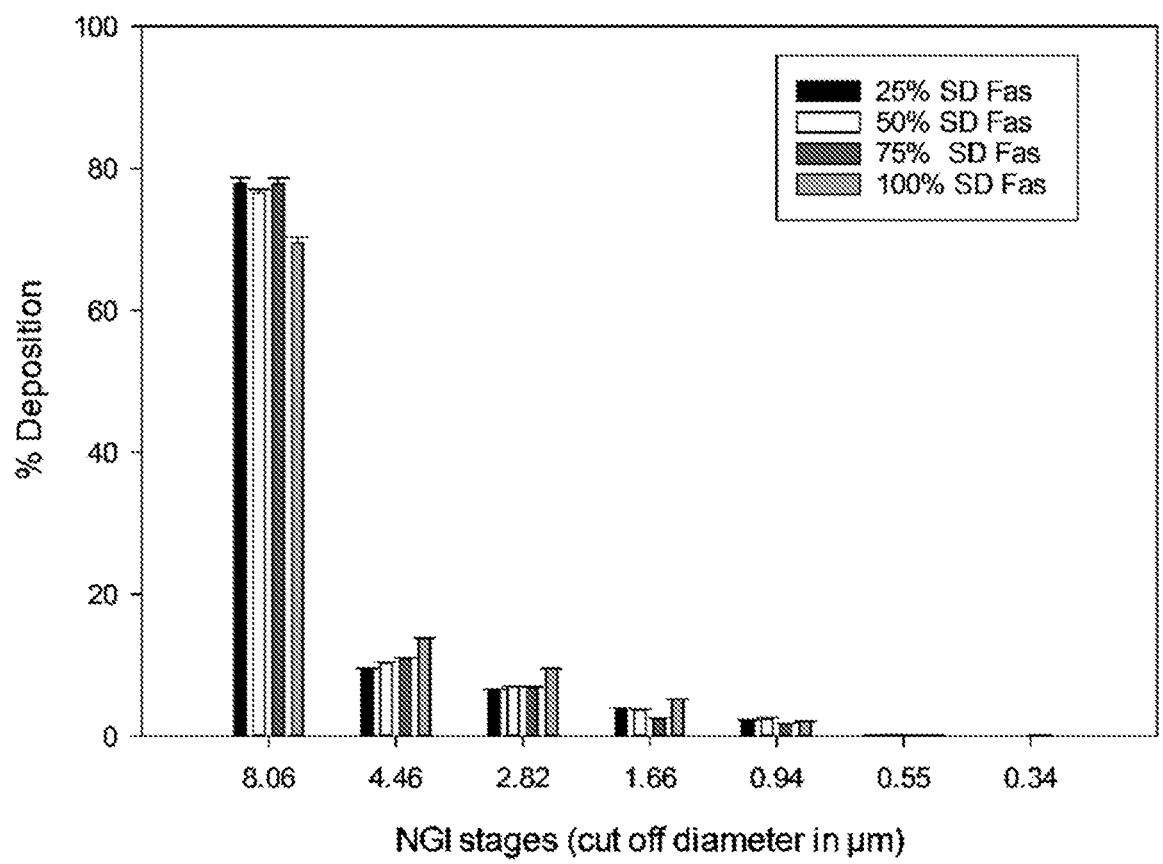

The in vitro aerosol stage deposition profiles of the SD Fas particles are presented in FIG. 9. As can be seen from FIG. 9, the SD Fas particles had diverse deposition profile when different inhaler devices were used. Aerolizer® and Neohaler® had more deposition on lower stages compared to Handihaler®. When comparing the aerosol properties from Table 5 all the devices had 80% or more of ED for all the SD Fas powders. The lowest MMAD that was less than between 6.5-7 μm was obtained using Aerolizer® with 50%, 75%, and 100% SD Fas powders. Neohaler®, when used with 75% SD Fas, produced the highest FPF of ~38%, followed by Aerolizer® with 50% SD Fas.

In Vitro Drug Dose-Response Cell Viability

Figure 10:
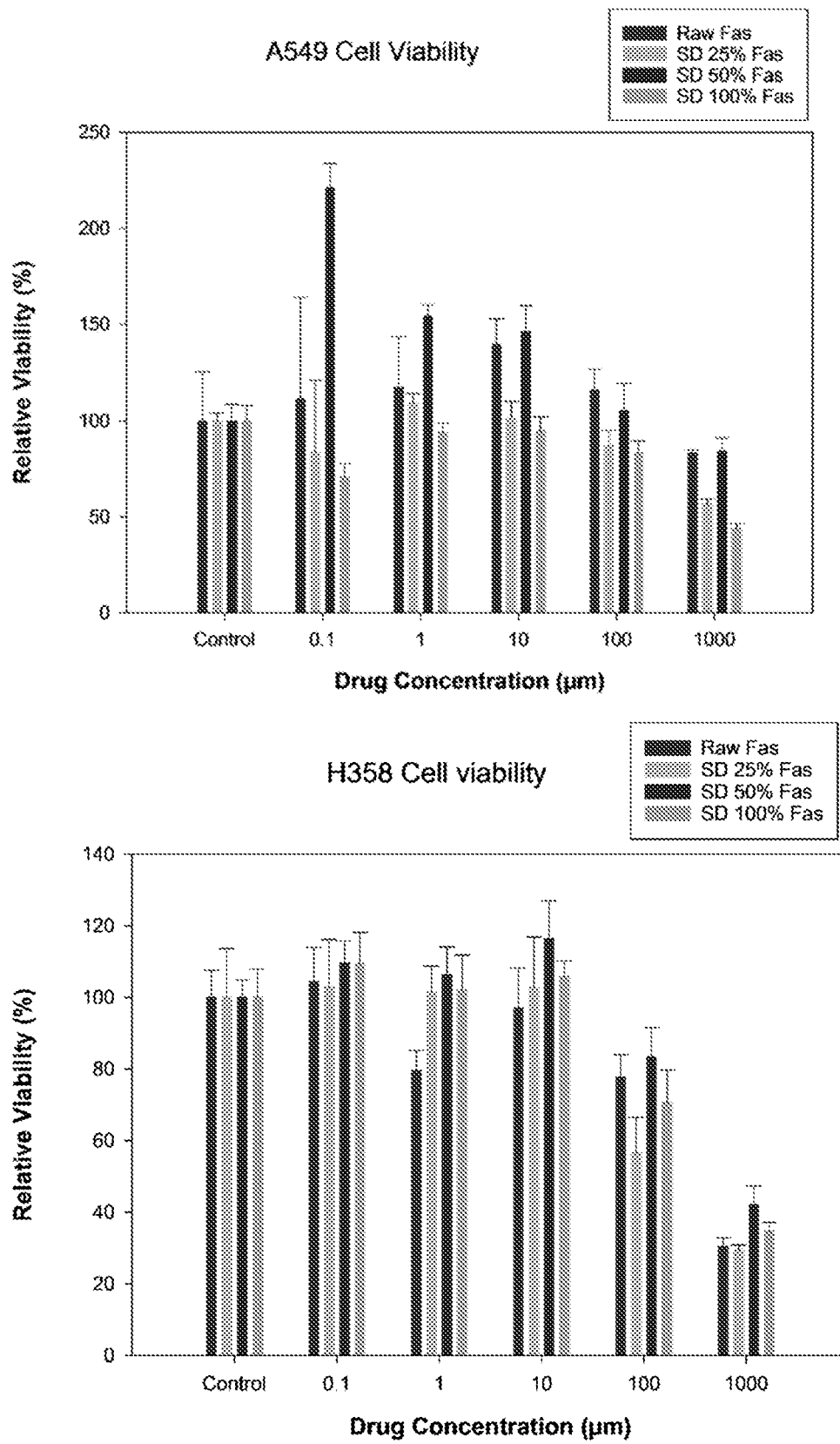
FIG. 10: In vitro Cell Viability of raw and selected SD Fas formulations using A549, H358 and Calu-3 pulmonary cell lines.
Figure 10:
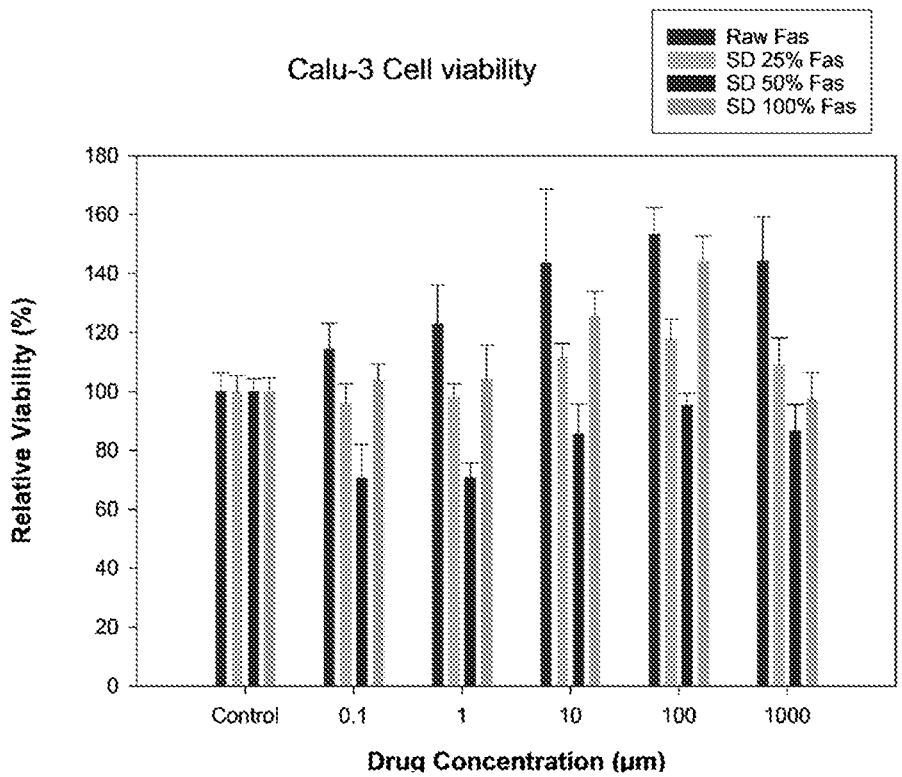

In vitro cell viability assay was performed on three human pulmonary cell lines: A549, H358, and Calu-3. Molar concentrations of 0.1, 1, 10, 100 and 1000 μM raw and selected SD Fas powders were tested (FIG. 10). Viability of A549 was higher at lower concentrations than the higher concentration of some SD fas powders. 25% and 100% SD Fas powders had lower viability at 0.1 μM compared to 1 μM. However, at higher concentrations of 100 μM and 1000 μM, the cell viability decreased. On the H358 cell lines, the cell viability decreased at higher concentrations for all the powders. In contrast, Calu-3 cell line had a viability higher than 95% when treated with all the SD formulations at all concentrations except 50% SD Fas. The viability of this Calu-3 was decreased by significantly by the SD fas powders at 50% PR.

In Vitro Transepithelial Electrical Resistance Analysis

Figure 11:
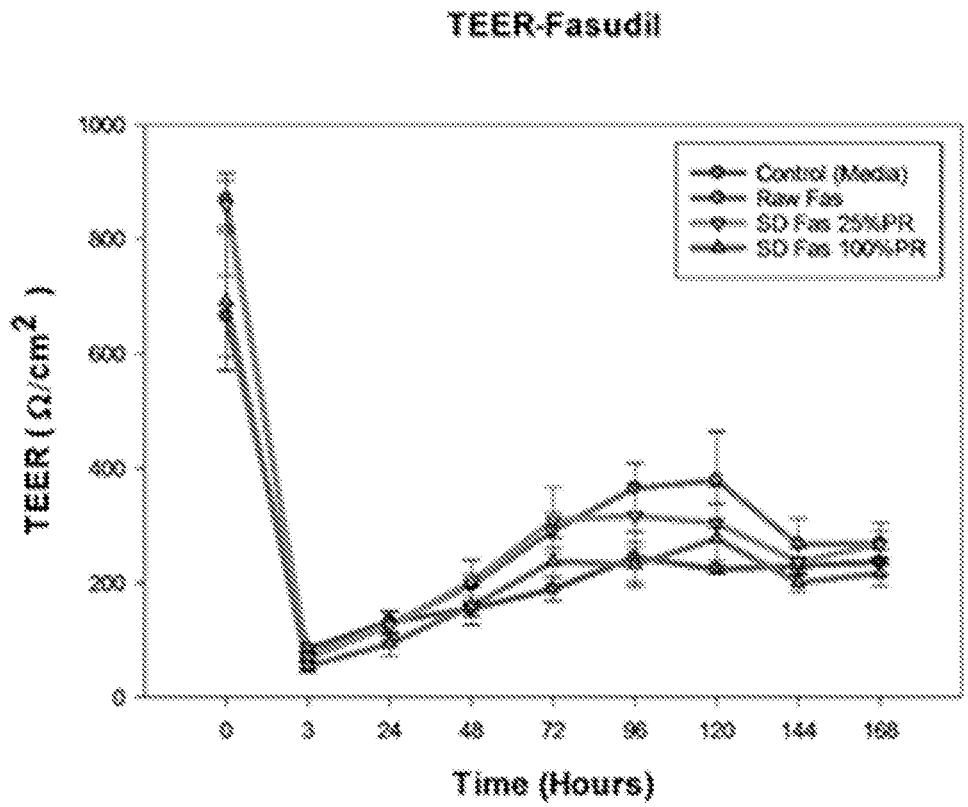
FIG. 11: Transepithelial Electrical Resistance (TEER) measurements of Raw and selected SD Fas formulations.

FIG. 11 displays the results of TEER measurement of Calu-3 cell line for seven days after treating with selected formulations of Fas. A concentration of 100 μm of the selected formulations were tested. All tested formulations had an acute reduction of transepithelial electrical resistance few hours after treatment. However, in the following days, the electrical resistance increased gradually similar to the control value which was treated with the cell culture media.

This study clearly demonstrates the ability to particle engineer Fas to an inhalable powder to treat pulmonary diseases. Spray dried drug decreases the treatment burden of inhaled powder mass. This study utilized a dilute solution of Fas in methanol which caused the formation of small spherical particles as seen from the SEM micrographs. As seen from the SEM micrographs, individually spray dried Fas formed small nanoaggregates/nanospheres. There was a pump rate effect noticed on the size and shape of these particles. At lower pump rates of 25% and 50%, the particles were smaller and spherical compared to the particles at higher pump rates of 75% and 100%. The sphericity of the particles changed as the pump rate increased, this pattern could be due to the difference in the feed rate of the solution which in turn affects the residence time of the particles in the primary spray drying chamber.

As for the thermal property of the powder, DSC data and HSM images are in general agreement for all samples except the SD Fas at 100% pump rate, where DSC showed a glass transition before melting that was not observed in HSM with a corresponding change in birefringence. From Table 3, it can be noted that the change in the heat capacity decreases with increasing spray drying pump rate. The minimal change in heat capacity at 100% PR can be a reason that the change in birefringence was not observed during HSM. It should also be noted that the conditions are not the same for DSC and HSM, DSC is performed under hermetically sealed pan while HSM is performed under open atmosphere. Previously, it has been reported that Fas has several polymorphic phases including a hemihydrate and a trihydrate (Hiromu Kawakubo; U.S. Pat. No. 5,942,505 1999), where the hemihydrate was found to be the stable form. It is possible that the compound underwent transitions from one form to the other during these observed stages. Overall, all SD particles didn't possess birefringence before the transition, indicating amorphous character, which is consistent with the DSC and XRPD results. Chemical characterization of fas in the spray dried sample was confirmed by elemental analysis of EDX where the distinctive peaks corresponding to S, 0, and Cl were seen. ATR-FTIR and Raman analysis further supported this by showing the characteristic absorption bands in the fingerprint region.

An important characteristic for inhalable powders is the residual water content. It was found that the water content was less than 3.5% for all spray dried samples. The reduced water content in inhalation powder can increase the shelf-life and aerosol performance of the particles.

Figure 12:
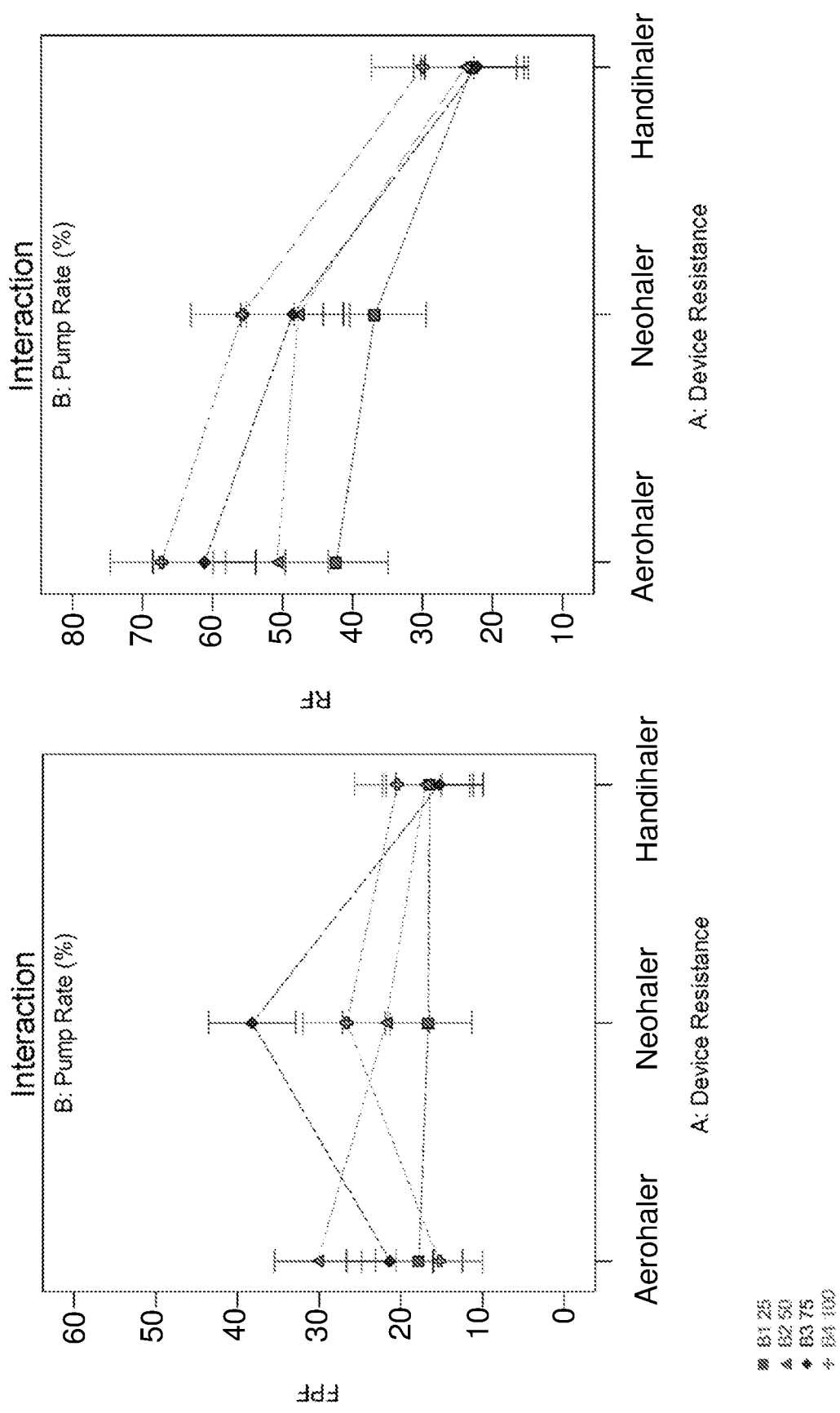
FIG. 12: Design of Experiments interaction plot comparing the effect of spray drying pump rate and inhaler device resistance on the aerosol performance. Plot generated using Design Expert® software.
Figure 12:
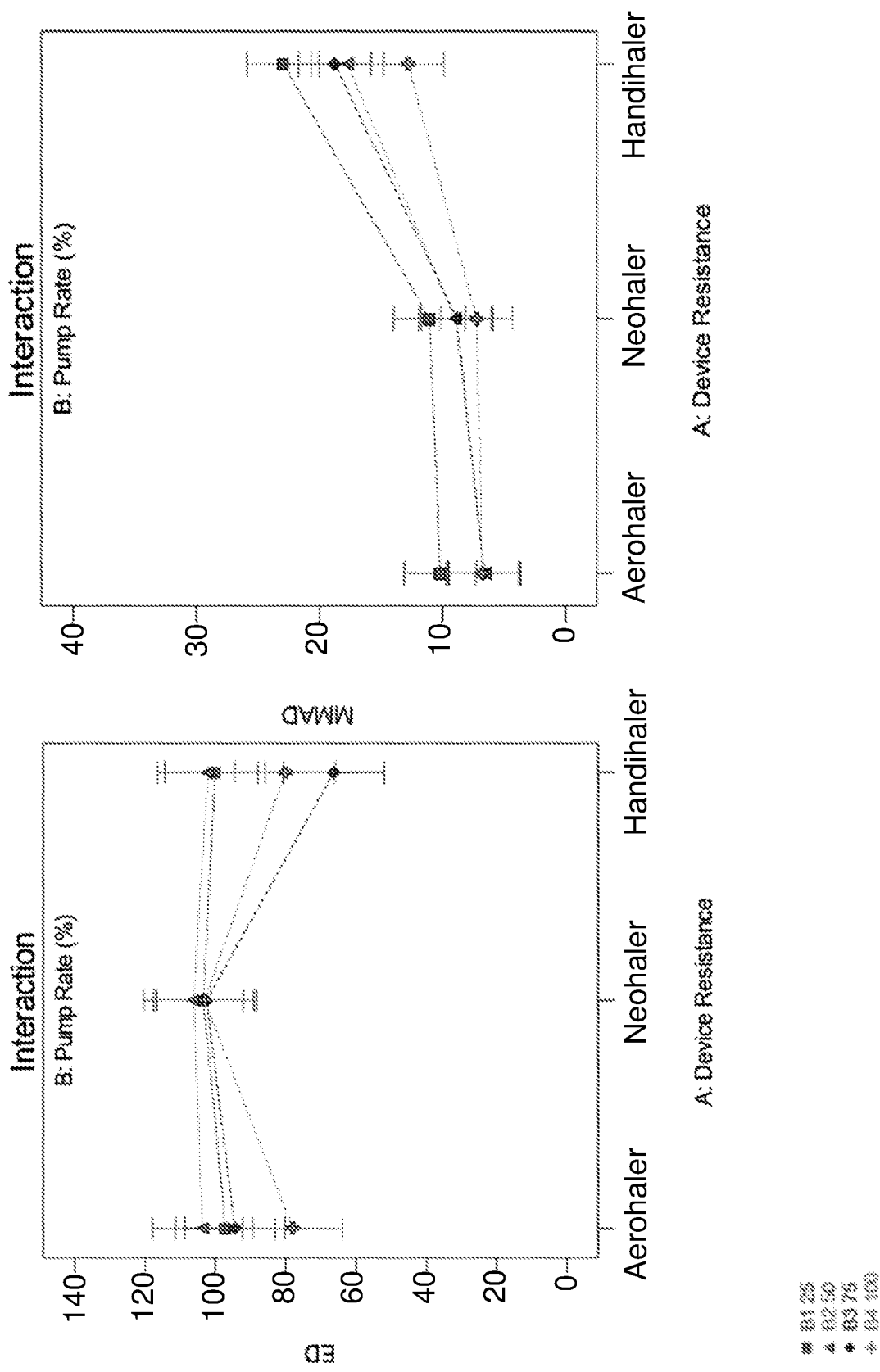
Figure 13:
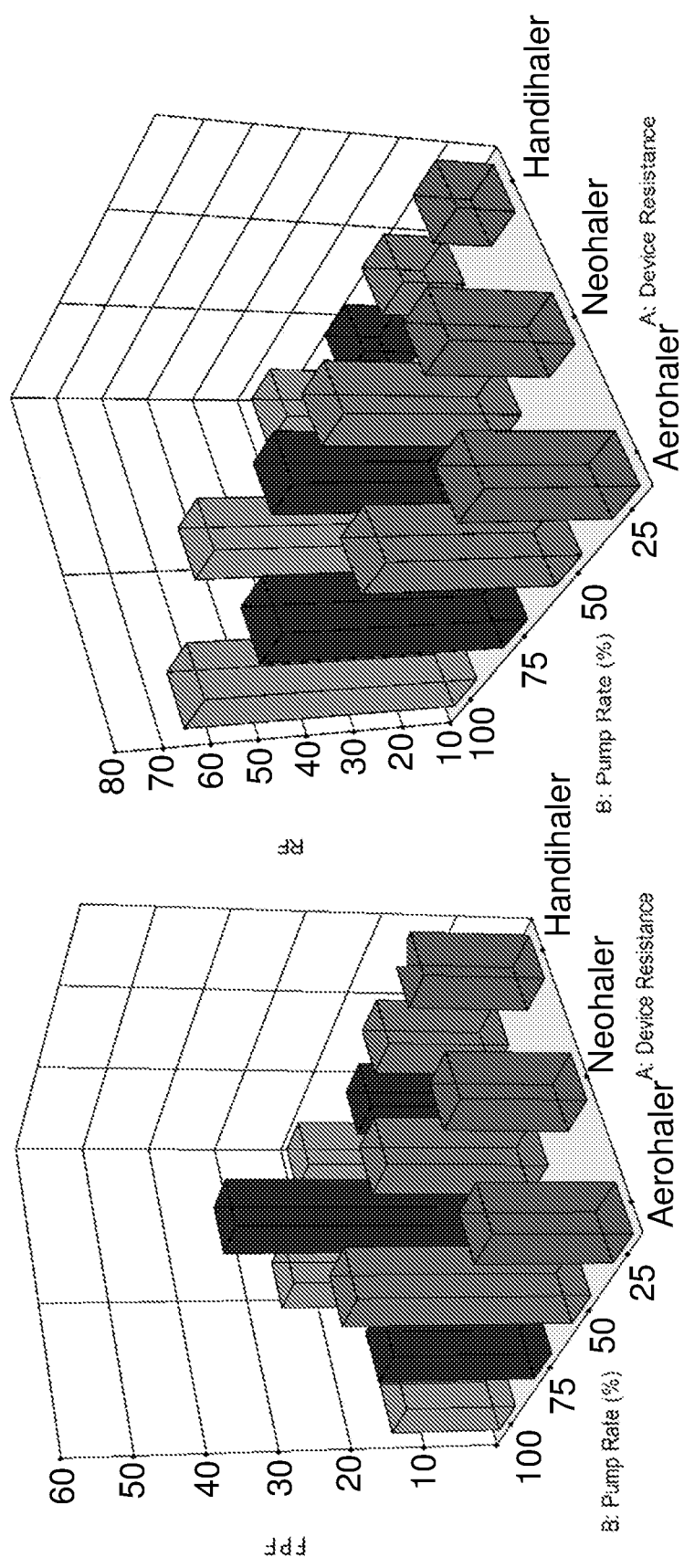
FIG. 13: Design of Experiments 3-D surface plots showing the effect of spray drying pump rate and inhaler device resistance on the aerosol performance. Plot generated using Design Expert® software.
Figure 13:
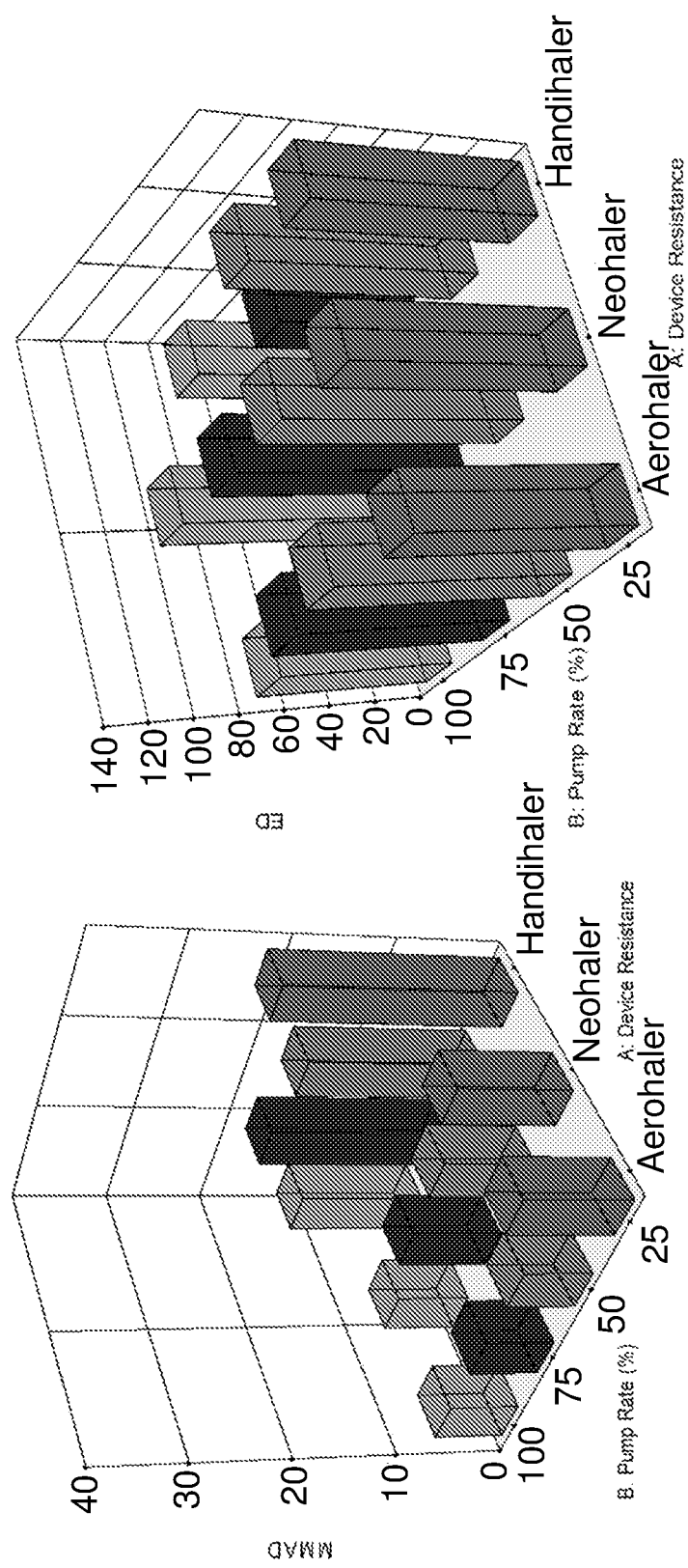

The factors interaction plots seen in FIGS. 12 and 13 show the interaction of spray drying pump rate and the DPI devices resistance influence on the aerosol dispersion of the SD Fas particles. From these graphs, it can be seen that all the SD Fas at different pump rates had the same or lower FPF when Handihaler was used. However, the FPF value is increased for some pump rates with low resistance device while for the other pump rates with medium resistance device.

The in vitro cellular studies show that the Fas formulation is safe to the pulmonary cell lines at selected concentrations. Student t-tests were performed to compare the cell viability of the formulations to that of the control group. It showed that the effect of the formulations were different with different cell lines. For example, 25% SD Fas at concentrations 100 and 1000 μM had statistically significant results in both A549 and H358 cell lines. While concentration of 1 μM the difference in the means was statistical significant only for A549 but not for H358. Similarly, cell viability results of SD 50% was statistically significant at concentrations 0.1, 1, 10 and 1000 μM for A549 while concentrations 0.1, 10, 100 and 1000 μM for H358. On the other hand, SD 100% showed statistically significant results at concentrations 0.1, 100 and 1000 μM for A549 and at concentrations 100 and 1000 μM for H358. This assay measures the fluorescence intensity of a metabolite of resazurin, any other compound that fluorescence can interfere with the measurement of the meatabolite. Since it was seen in Raman spectroscopy that Fas can fluorescence, there is a possibility of interference from the compound. After 7 days the TEER values value reached the same value as naïve cells, indicating a reversible disruption of the monolayer of the cells treated with the drug.

TABLE 1

Advanced spray drying parameters for spray dried (SD) Fasudil powders at a feed concentration of 0.5% w/v from methanol (MeOH) solution.

| Pump Rate (%) | Inlet T(° C.) | Outlet T(° C.) |
|---|---|---|
| 25 | 149-152 | 76-88 |
| 50 | 150-151 | 67-68 |
| 75 | 150-151 | 55-65 |
| 100 | 150-152 | 43-56 |

The drying gas atomization rate (670 L/h at 35 mmHg) and aspiration rate (35 m3/h at 100% rate) was maintained constant during all the experiments. Four feed input rates were employed to obtained particles using pump rates of 7.5 mL/min (25%), 15 mL/min (50%), 22.5 mL/min (75%) and 30 mL/min (100%). The stainless steel two-fluid nozzle tip diameter was 0.7 mm with 1.5 mm gas cap.

TABLE 2

Particle sizing using image analysis on SEM micrographs (n ≥ 100 particles)

| Spray Drying Pump Rate (%) | Size Range (μm) | Mean Size (μm) |
|---|---|---|
| 25 | 0.27-1.677 | 0.068 ± 0.023 |
| 50 | 0.343-1.938 | 0.855 ± 0.302 |
| 75 | 0.346-3.199 | 1.075 ± 0.510 |
| 100 | 0.454-2.778 | 1.168 ± 0.507 |

TABLE 3

DSC thermal analysis. (n = 3, mean ± standard deviation)

| Powder Identification | Spray Drying Pump Rate (%) | $T_{peak}$ (° C.) | ΔH (J/g) | $Tg_{(peak)}$ (° C.) | ΔCp (J/g° C.) |
|---|---|---|---|---|---|
| Raw Fas | N/A | 137.19 ± 0.19 | 55.06 ± 3.29 | N/A | N/A |
|  |  | 159.86 ± 4.94 | 16.93 ± 3.62 |  |  |
|  |  | 215.01 ± 0.30 | 105.5– ± 2.89 |  |  |
| SD Fas | 25 | 86.10 ± 1.91 | 45.35 ± 3.09 | 46.91 ± 1.05 | 1.33 ± 0.17 |
|  |  | 209.28 ± 0.71 | 88.18 ± 12.69 |  |  |
| SD Fas | 50 | 106.66 ± 0.79 | 41.54 ± 11.58 | 47.07 ± 0.44 | 1.15 ± 0.44 |
|  |  | 209.47 ± 0.37 | 8.54 ± 2.04 |  |  |
|  |  | 215.79 ± 0.36 | 44.26 ± 14.19 |  |  |
| SD Fas | 75 | 108.13 ± 0.99 | 41.50 ± 5.76 | 49.47 ± 3.42 | 0.49 ± 0.17 |
|  |  | 210.52 ± 0.54 | 45.81 ± 7.8 |  |  |
|  |  | 216.61 ± 0.42 | 23.59 ± 1.60 |  |  |
| SD Fas | 100 | 76.25 ± 3.26 | 39.13 ± 8.46 | 51.80 ± 1.34 | 0.50 ± 0.22 |
|  |  | 186.84 ± 20.81 | 16.66 ± 0.22 |  |  |
|  |  | 211.51 ± 2.07 | 34.48 ± 5.49 |  |  |

TABLE 4

Residual water content quantified by KFT. (n = 3, mean ± standard deviation)

| Powder Identification | Spray Drying Pump Rate (%) | Residual Water content (% w/w) |
|---|---|---|
| Raw Fas | N/A | 2.97 ± 0.06 |
| SD Fas | 25 | 3.22 ± 0.56 |
| SD Fas | 50 | 2.57 ± 0.36 |
| SD Fas | 75 | 2.45 ± 0.49 |
| SD Fas |  |  |
| SD Fas | 100 | 2.73 ± 0.57 |
| SD Fas |  |  |

TABLE 5

In vitro aerosol dispersion performance of SD Fas powders at four different pump rates using the FDA-approved human DPI devices, Aerolizer ®, Neohaler ® and Handihaler ® (n = 3, mean ± standard deviation)

|  | Aerolizer ® | Neohaler ® | Handihaler ® |
|---|---|---|---|
| SD Fas 25% | | | |
| FPF | 17.79 ± 3.78 | 16.63 ± 4.78 | 16.65 ± 1.76 |
| RF | 42.28 ± 22.14 | 36.82 ± 17.75 | 22.17 ± 2.67 |
| ED | 97.16 ± 2.86 | 103.49 ± 1.26 | 98.56 ± 2.49 |
| MMAD | 10.18 ± 5.26 | 11.07 ± 5.25 | 22.33 ± 7.06 |
| GSD | 2.38 ± 0.36 | 2.78 ± 0.26 | 3.58 ± 0.57 |
| SD Fas 50% | | | |
| FPF | 30.16 ± 3.74 | 21.83 ± 5.94 | 16.53 ± 3.06 |
| RF | 50.79 ± 22.19 | 47.78 ± 22.94 | 23.36 ± 2.15 |
| ED | 103.71 ± 2.76 | 106.29 ± 3.17 | 99.58 ± 0.44 |
| MMAD | 6.53 ± 2.87 | 9.00 ± 4.49 | 17.83 ± 1.60 |
| GSD | 2.2 ± 0.22 | 2.37 ± 0.38 | 3.27 ± 0.05 |
| SD Fas 75% | | | |
| FPF | 21.35 ± 7.05 | 38.21 ± 10.42 | 15.2 ± 0.59 |
| RF | 61.15 ± 27.24 | 48.59 ± 21.79 | 20.07 ± 4.05 |
| ED | 94.52 ± 10.42 | 102.59 ± 1.52 | 92.64 ± 6.62 |
| MMAD | 6.62 ± 2.98 | 8.84 ± 3.86 | 18.77 ± 0.44 |
| GSD | 2.38 ± 0.31 | 2.12 ± 0.477 | 3.15 ± 0.20 |
| SD Fas 100% | | | |
| FPF | 15.32 ± 1.44 | 26.65 ± 7.83 | 21.082 ± 1.40 |
| RF | 67.27 ± 29.31 | 55.74 ± 24.88 | 30.83 ± 2.23 |
| ED | 78.07 ± 1.52 | 103.12 ± 0.98 | 80.57 ± 8.97 |
| MMAD | 6.77 ± 3.11 | 7.22 ± 3.15 | 12.54 ± 1.11 |
| GSD | 1.86 ± 0.33 | 2.15 ± 0.18 | 3.04 ± 0.41 |

Example 2

Fasudil hydrochloride was co-spray dried with mannitol using the conditions in Table 6. The particles were comprehensively characterized and in vitro aerosol dispersion performance using three different inhaler devices were tested. Molecular mixtures of fasudil and mannitol were successfully formulated and inhalable as dry powders.

TABLE 6

Advanced spray drying parameters for co-spray dried (co-SD) Fas:Man powders from methanol (MeOH) using organic solution advanced closed mode spray drying particle engineering design.

| Powder Composition (Molar Ratio) | Molar Ratio Composition (Fas:D-Man) | Feed concentration in MeOH (% w/v) | Pump Rate (%) | Inlet T (° C.) | Outlet T (° C.) |
|---|---|---|---|---|---|
| Co-SD Fas:D-man | 30:70 | 0.168 | 25 | 150-152 | 91-96 |
| Co-SD Fas:D-man | 30:70 | 0.168 | 50 | 149-150 | 70-77 |
| Co-SD Fas:D-man | 30:70 | 0.168 | 75 | 149-150 | 55-61 |
| Co-SD Fas:D-man | 30:70 | 0.168 | 100 | 149-152 | 44-52 |

Results
SEM—EDX

Figure 14:
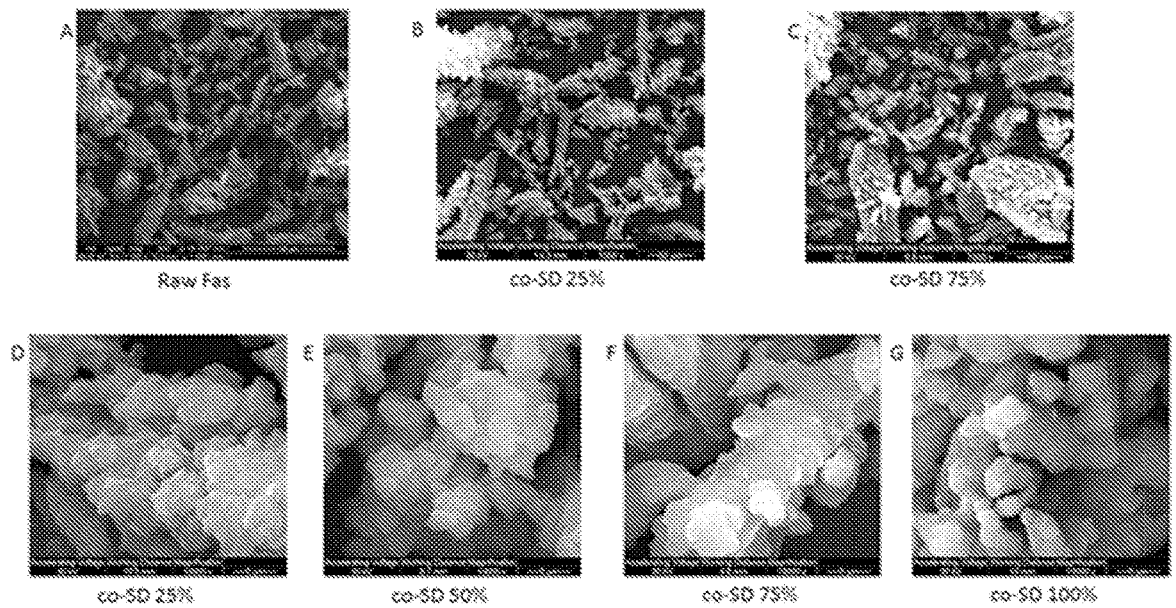
FIG. 14: SEM micrographs of Raw Fasudil hydrochloride and co-SD fas: man at 1,000× magnification: A—raw fas, B—co-SD 25% pump rate, C—co-SD 75% pump rate; at 10,000× magnification D—co-SD 25% pump rate, E—co-SD 50% pump rate, E—co-SD 75% pump rate, F—co-SD 100% pump rate.

The co-SD particles, at a lower magnification (<1000×) particles from all pump rates, appeared to be elongated or rod-shaped. However, on higher magnification, it was possible to identify that the elongated rods were indeed aggregation of smaller particles (FIG. 14). The smaller particles were irregular in shape with a slightly rough surface.

Figure 15:
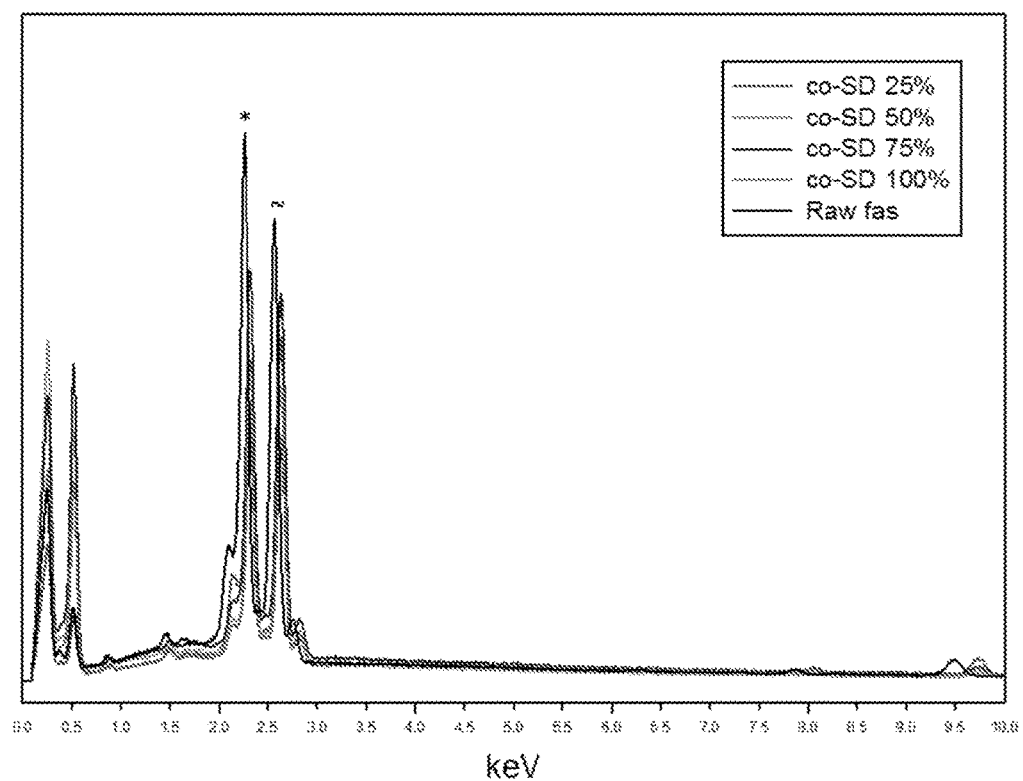
FIG. 15: EDX spectra of raw and co-SD fas:man samples showing characteristic peaks of * sulfur (S) and ~chlorine (Cl) atom.
Figure 16:
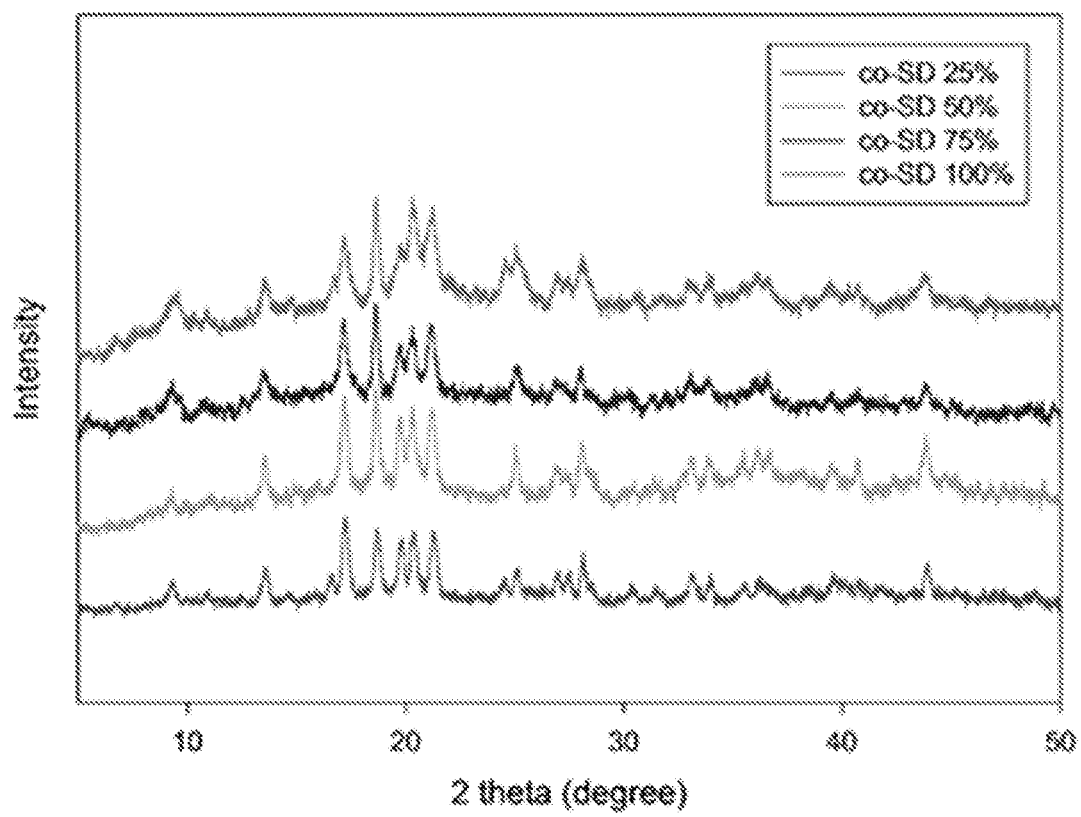
FIG. 16: XRPD diffraction patterns of Co-SD Fas:D-Man at all spray drying pump rate.
Figure 17:
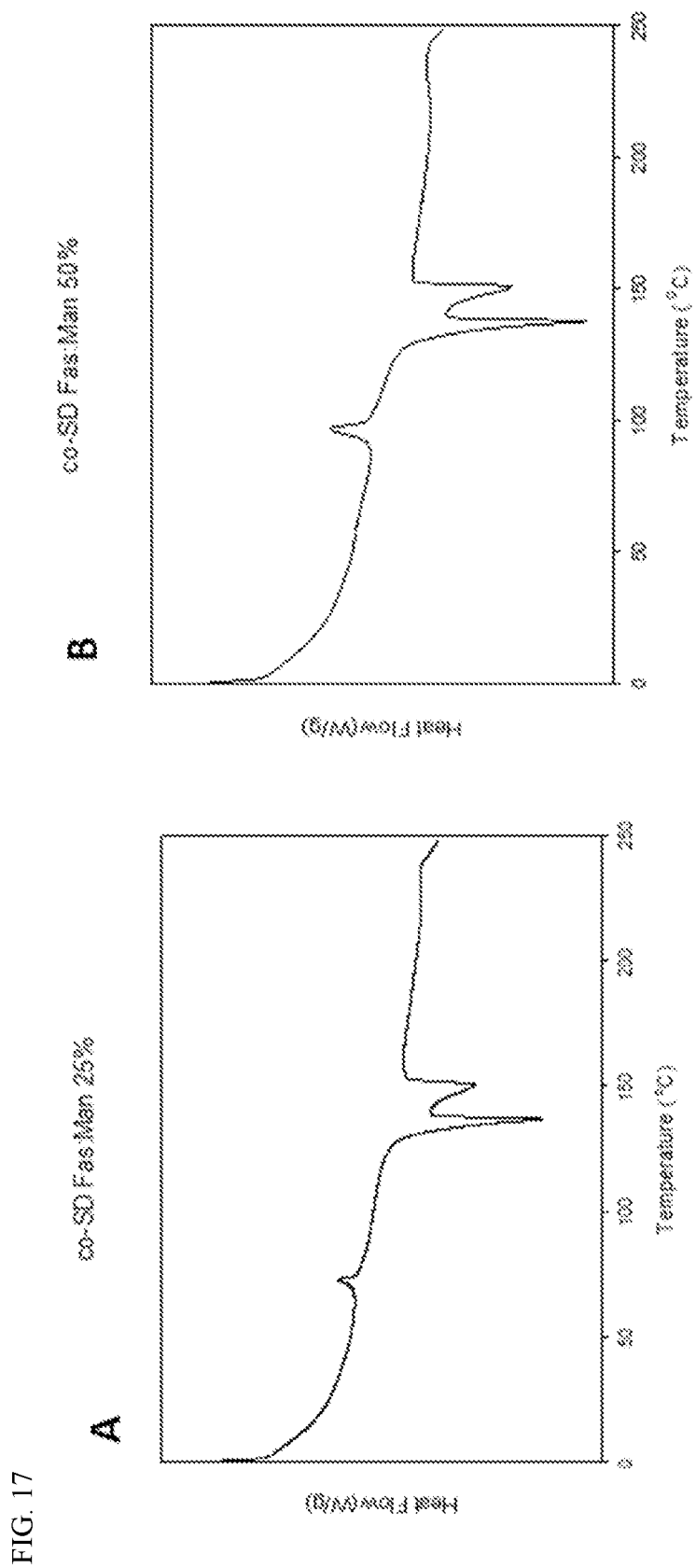
FIG. 17: Representative DSC thermograms of A—co-SD Fas 25% pump rate, B—co-SD fas 50% pump rate, C—co-SD Fas 75% pump rate, D—co-SD Fas 100% pump rate
Figure 17:
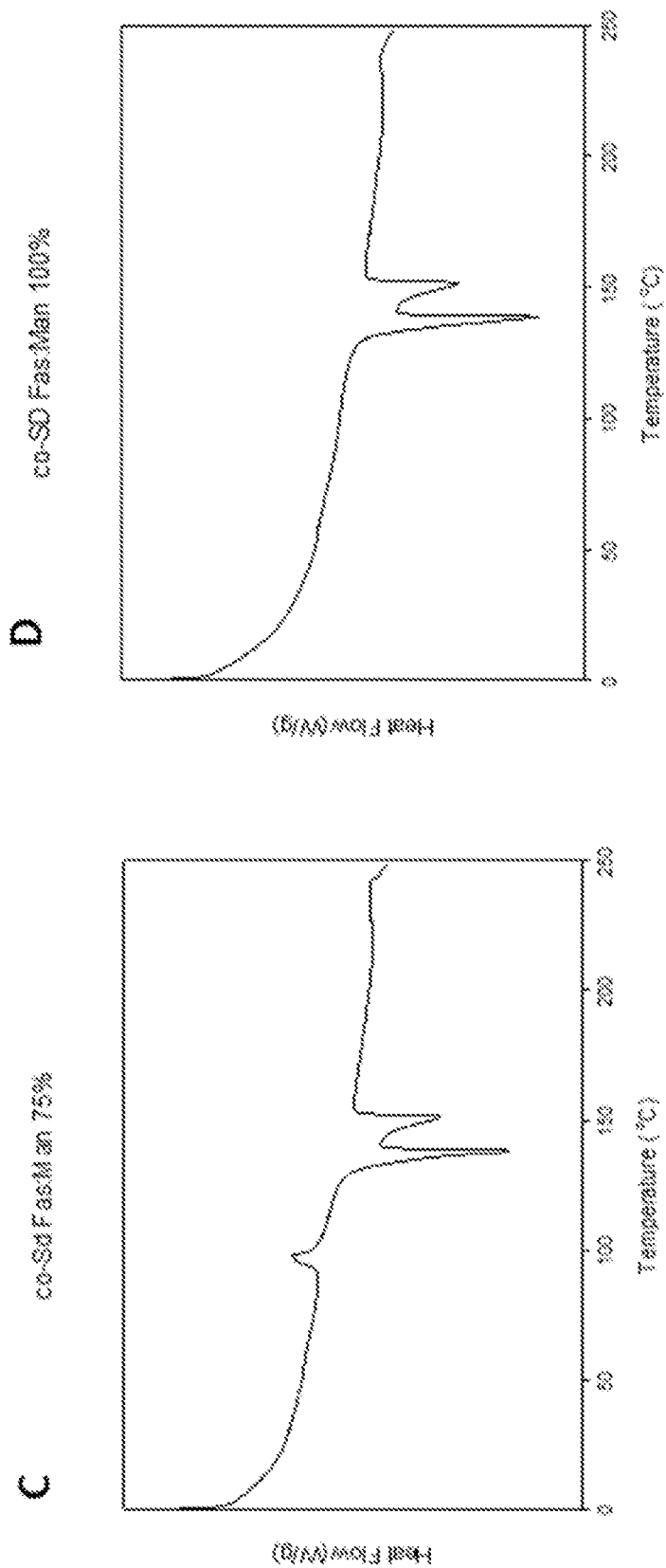

The energy dispersive X-ray (EDX) spectra of the powders are shown in FIG. 15. For chemical identification of Fas, the characteristic Kα line (peaks) of Sulphur (S) is seen at 2.3 keV and the Kα line of chlorine (Cl) is seen at 2.63 keV. The Kα lines of carbon (C) at 0.257 keV and oxygen (O) at 0.526 keV obscure the peaks of nitrogen (N) which is usually seen at 0.392 keV. Hence, identifying N was not selected as the characteristic element. The peaks corresponding to S and Cl are representative elements of Fas. All co-SD (FIG. 15) powders possess these peaks in their EDX spectrum, indicating the presence of Fas as an acid salt before and after spray drying.

Laser Diffraction Particle Size Analysis

The laser diffraction particle size analysis was performed on raw Fas and all co-SD samples. The results of laser diffraction particle size distribution measurements are presented in Table 7. As can be seen from the table, the mean volumetric diameter $D_{v50}$ of raw Fas was about 5 μm, while that of co-SD samples ranged from 4.6-4.7 μm. This is verified by the SEM micrographs of co-SD Fas:Man particles where the smaller particles aggregated to form elongated particles.

previously reported diffraction pattern (i, F. G. Vogt, D. Hayes, Jr., H. M. Mansour, Design, characterization, and aerosol dispersion performance modeling of advanced spray-dried microparticulate/nanoparticulate mannitol powders for targeted pulmonary delivery as dry powder inhalers, Journal of aerosol medicine and pulmonary drug delivery, 27 (2014) 81-93). The characteristic peak 13.5° and 17.2° 2θ indicates that the co-SD D-Man was in the alpha form (i, F. G. Vogt, D. Hayes, Jr., H. M. Mansour, Design, characterization, and aerosol dispersion performance modeling of advanced spray-dried microparticulate/nanoparticulate mannitol powders for targeted pulmonary delivery as dry powder inhalers, Journal of aerosol medicine and pulmonary drug delivery, 27 (2014) 81-93). No peaks corresponding to Fas were observed in the co-SD Fas:Man powders at all pump rates.

Differential Scanning Calorimetry (DSC)

Among the co-SD Fas:Man particles engineered at pump rates (PR), 25% PR, 50% PR, and 75% PR exhibited an exotherm between 73-98° C., followed by two endothermic transitions (FIG. 17 and Table 8). While 100% PR exhibited only two endothermic transitions around 138° C. and 152° C. This indicates that except 100% PR, co-SD Fas:Man particles from other pump rates undergo a thermodynamic transition before melting. It is noted that the endothermic transitions of co-SD Fas:Man particles are seen in the melting range of D-mannitol, the excipient used in the study and that the melting of Fas at a temperature above 200° C. was not observed in any co-SD Fas:Man powder. However,

TABLE 7

Particle sizing using laser sizing (n = 3, mean ± standard deviation)

| Powder Composition (Molar Ratio) | Spray Drying Pump Rate (%) | $D_{v10}$ (μm) | $D_{v50}$ (μm) | $D_{v90}$ (μm) | Span Value |
|---|---|---|---|---|---|
| Raw FH | N/A | 3.67 ± 0.32 | 4.96 ± 3.5 | 7.42 ± 0.19 | 0.765 ± 0.15 |
| Co-SD Fas:D-man 30:70 | 25 | 3.43 ± 0.00 | 4.70 ± 0.01 | 8.04 ± 0.29 | 0.98 ± 0.6 |
| Co-SD Fas:D-man 30:70 | 50 | 3.44 ± 0.02 | 4.72 ± 0.08 | 7.73 ± .007 | 0.91 ± 0.01 |
| Co-SD Fas:D-man 30:70 | 75 | 3.41 ± 0.00 | 4.59 ± 0.01 | 7.34 ± 0.04 | 0.856 ± 0.01 |
| Co-SD Fas:D-man 30:70 | 100 | 3.41 ± 0.00 | 4.59 ± 0.02 | 7.40 ± 0.07 | 0.87 ± 0.01 |

X-Ray Powder Diffraction (XRPD)

As seen in FIG. 16, all co-SD Fas:Man samples exhibited peaks at 13.5°, 17.2°, 18.6°, 20.3° and 21.2° 2θ similar to there was no noticeable Tg identified for raw FH and co-SD Fas:Man particles as expected from its XRPD diffraction pattern.

TABLE 8

DSC thermal analysis. (n = 3, mean ± standard deviation)

| Powder Composition (Molar Ratio) | Spray Drying Pump Rate (%) | $T_{peak}$ (° C.) | ΔH (J/g) | $Tg_{(peak)}$ (° C.) | ΔCp (J/g° C.) |
|---|---|---|---|---|---|
| Co-SD Fas:D-man 30:70 | 25 | 73.25 ± 3.96<br>136.59 ± 0.81<br>150.60 ± 0.37 | 25.61 ± 28.12<br>40.00 ± 3.80<br>34.57 ± 2.18 | N/A | N/A |
| Co-SD Fas:D-man 30:70 | 50 | 97.76 ± 0.49<br>137.79 ± 0.18<br>151.19 ± 0.25 | 18.75 ± 1.78<br>51.26 ± 2.36<br>42.77 ± 1.22 | N/A | N/A |

TABLE 8-continued DSC thermal analysis. (n = 3, mean ± standard deviation)

| Powder Composition (Molar Ratio) | Spray Drying Pump Rate (%) | $T_{peak}$ (° C.) | ΔH (J/g) | $Tg_{(peak)}$ (° C.) | ΔCp (J/g° C.) |
|---|---|---|---|---|---|
| Co-SD Fas:D-man 30:70 | 75 | 94.57 ± 2.31<br>137.39 ± 0.38<br>151.19 ± 0.25 | 16.92 ± 2.47<br>48.60 ± 2.10<br>47.49 ± 3.88 | N/A | N/A |
| Co-SD Fas:D-man 30:70 | 100 | 138.02 ± 0.86<br>151.84 ± 0.09 | 53.25 ± 4.07<br>38.61 ± 4.53 | N/A | N/A |

Hot Stage Microscopy (HSM) Under Cross-Polarizers

Figure 18:
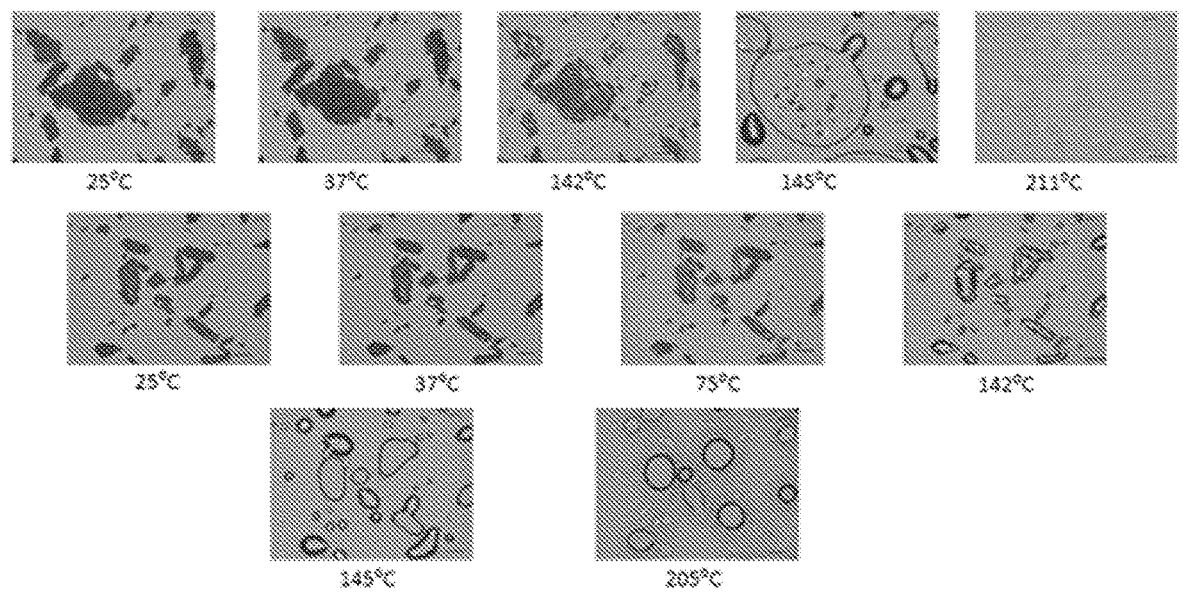
FIG. 18: Representative HSM images for: A—Raw Fas, B—SD fas 25% pump rate, C—SD Fas 100% pump rate, D—co-SD Fas 50% pump rate, E—co-SD Fas 75% pump rate.
Figure 19:
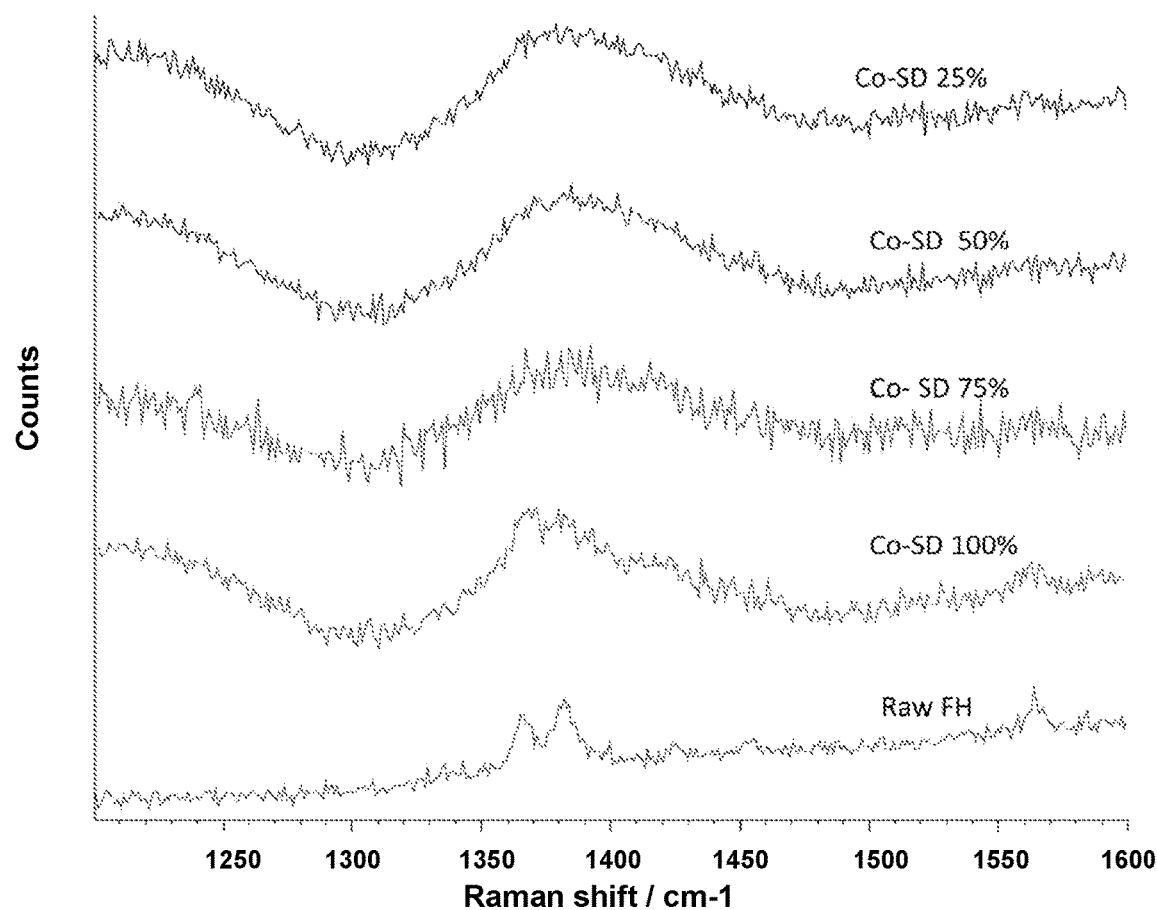
FIG. 19: Representative Raman spectra of raw and co-SD Fas:Man powders at different pump rates.

Co-SD Fas:Man at 25% pump rate exhibited a change in birefringence at about 103° C. and 144° C. before it melted at 147° C. Co-SD Fas:Man 50% (FIG. 18) showed a change in birefringence around 135° C. followed by melting at 145° C. Co-SD Fas:Man 75% showed a change in birefringence at around 75° C. followed by melting at 145° C. Co-SD Fas:Man at 100% showed a change in birefringence at around 143° C. before it melted at 149° C.

Hot Stage Microscopy (HSM) Under Cross-Polarizers

Co-SD Fas:Man at 25% pump rate exhibited a change in birefringence at about 103° C. and 144° C. before it melted at 147° C. Co-SD Fas:Man 50% (FIG. 18) showed a change in birefringence around 135° C. followed by melting at 145° C. Co-SD Fas:Man 75% showed a change in birefringence at around 75° C. followed by melting at 145° C. Co-SD Fas:Man at 100% showed a change in birefringence at around 143° C. before it melted at 149° C.

Attenuated Total Reflectance—FTIR Spectroscopy

Figure 20:
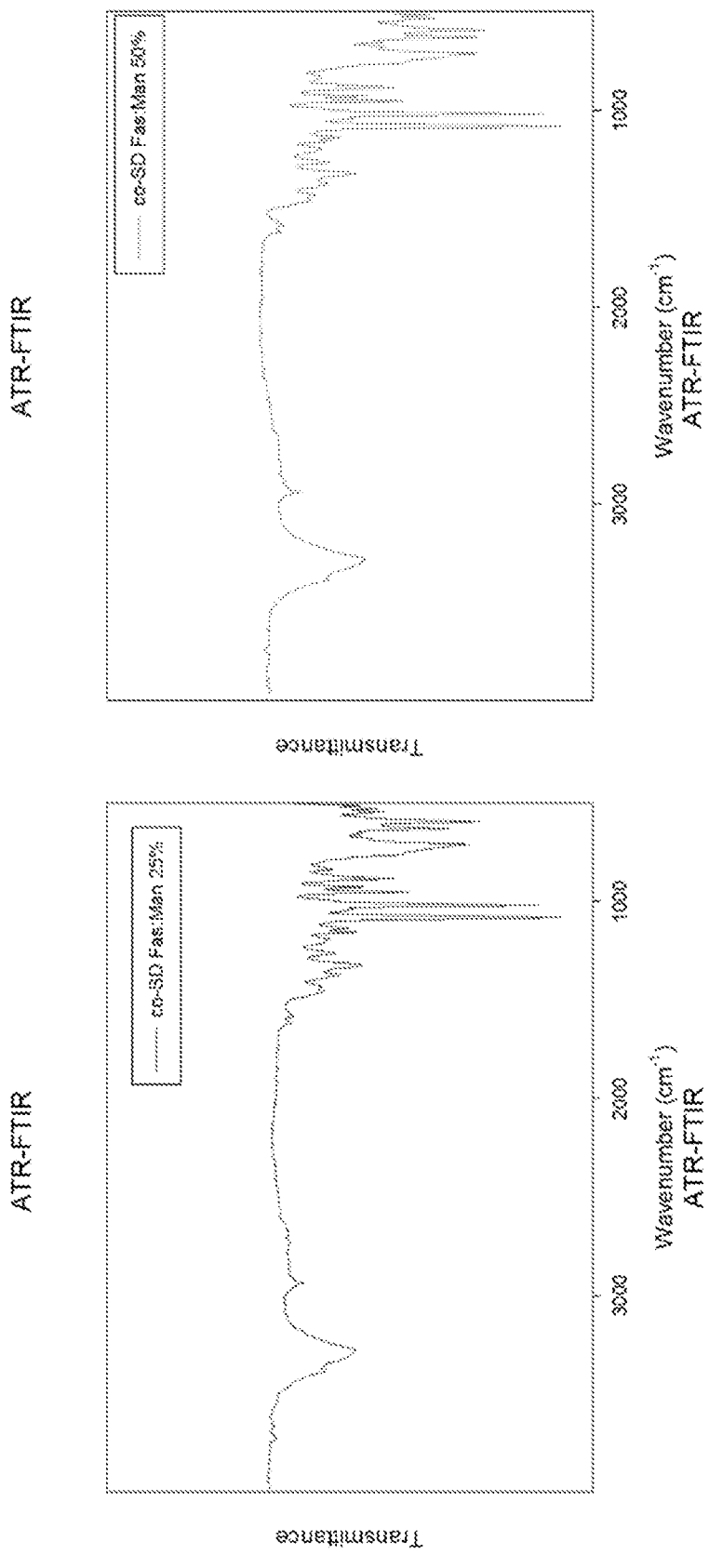
FIG. 20: ATR-FTIR spectrum of co-SD Fas:Man powders at different pump rates. In Vitro Aerosol Dispersion Performance
Figure 20:
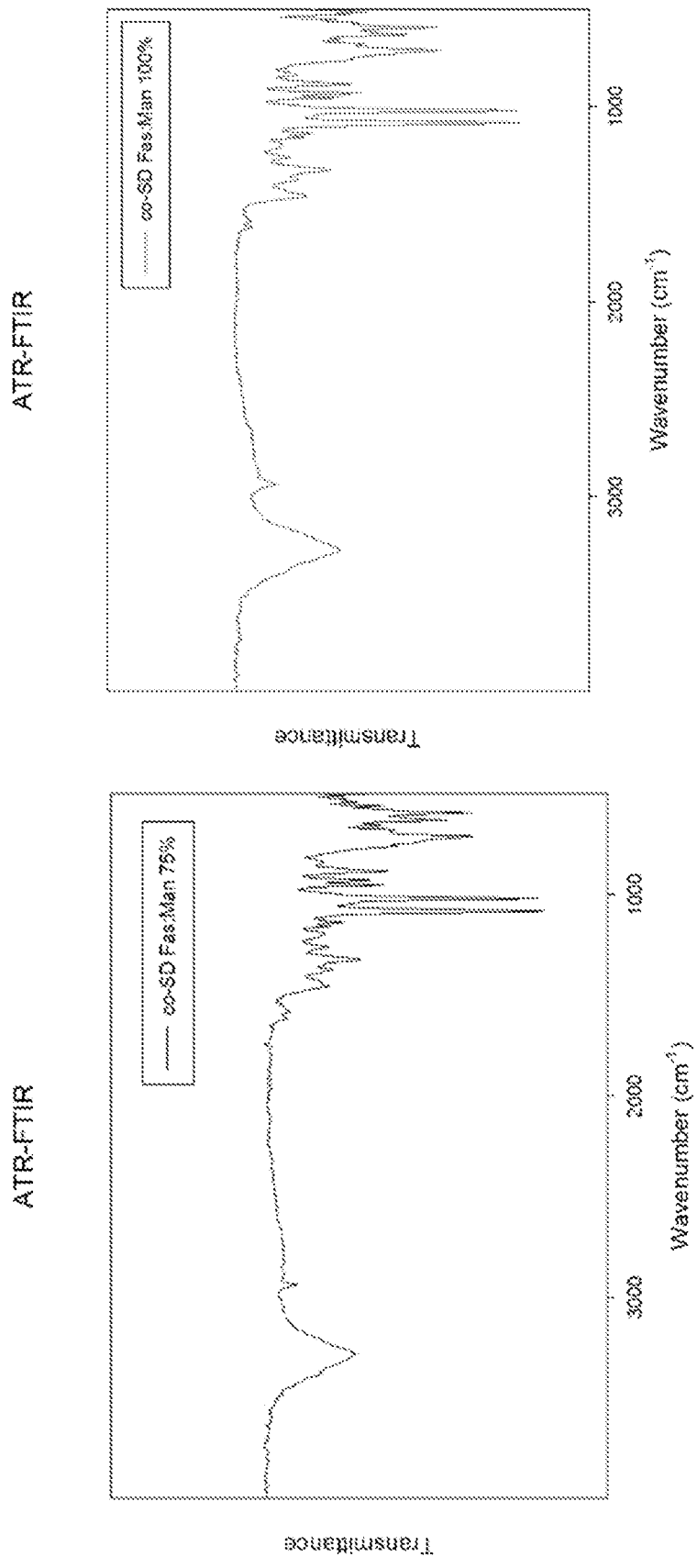

The spectral pattern seen at fingerprint region (<1500 wavenumber) was consistently observed in all co-SD and raw Fas samples where the peaks were found at approximately 710, 836, 892, 1012, 1136 and 1325 $cm^{-1}$. In FIG. 20, the co-SD Fas:Man systems at all pump rates exhibited an additional signal at approximately 3280 $cm^{-1}$ which is absent in SD Fas, indicating H-bonding with mannitol.

In Vitro Aerosol Dispersion Performance

Figure 21:
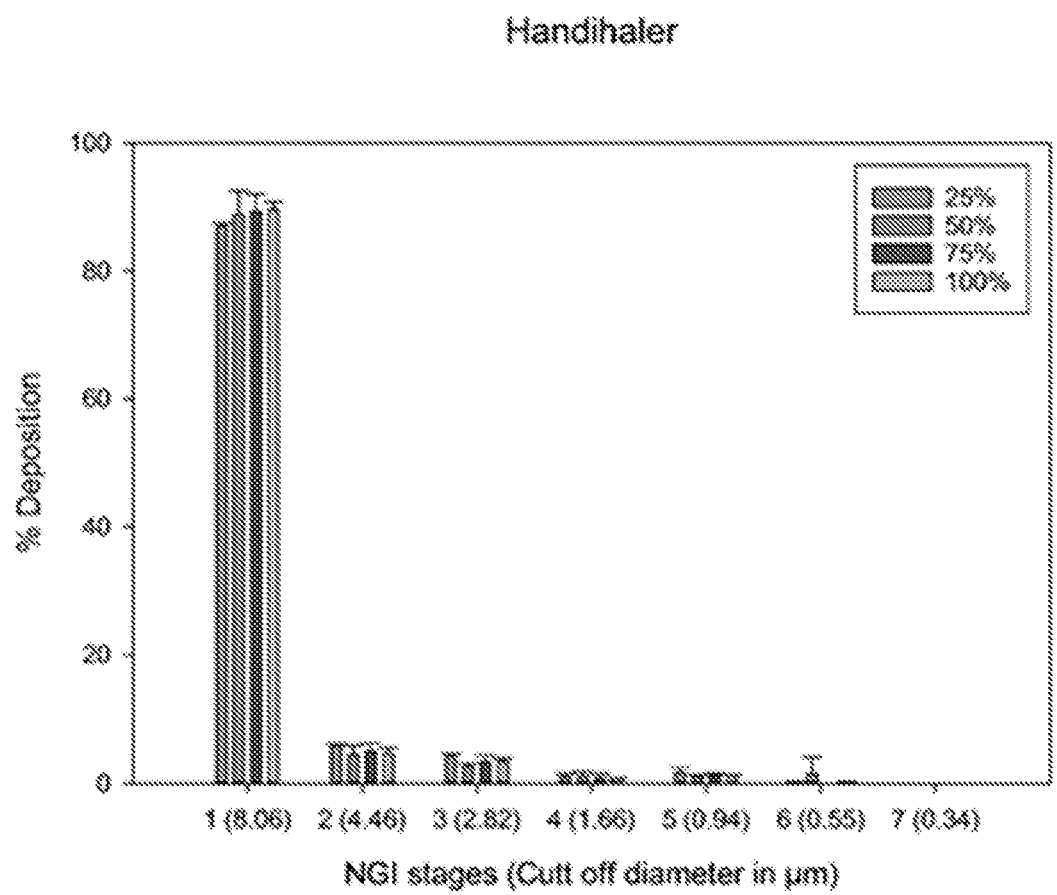
FIG. 21: In vitro aerosol dispersion performance of co-SD Fas powders at all pump rates using the NGI and the FDA-approved human DPI devices, Aerolizer®, Neohaler® and Handihaler®
Figure 22:
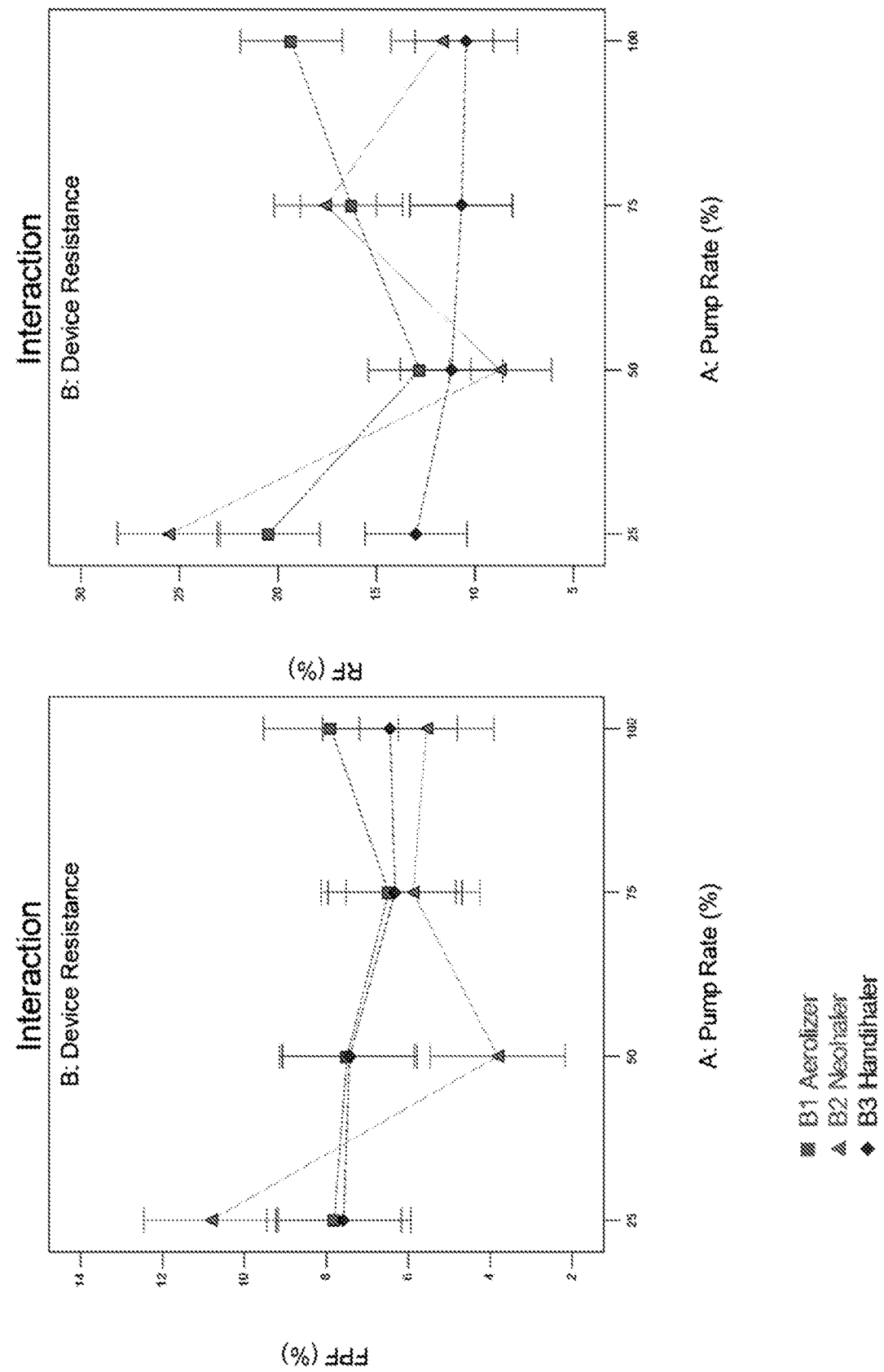
FIG. 22: Design of Experiments interaction plot comparing the effect of spray drying pump rate and inhaler device resistance on the aerosol performance of co-SD Fas:Man powders. Plot generated using Design Expert® software.
Figure 22:
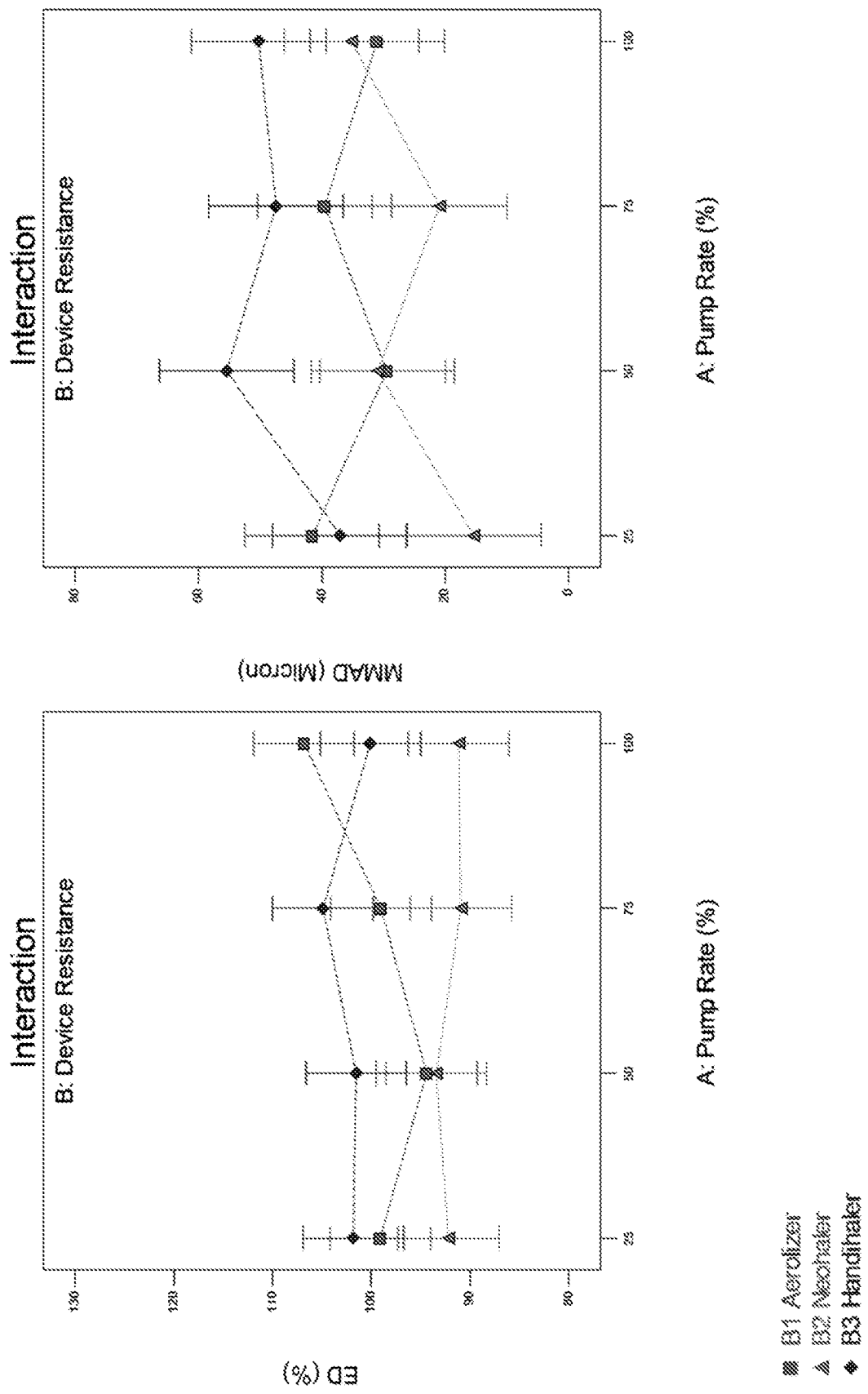

The NGI stage deposition of the co-SD Fas:Man particles made using four different pump rates are shown in FIG. 21. As can be seen in FIG. 22, the co-SD Fas particles had a slightly different deposition profile with the three different DPI devices. Nonetheless, majority of the particle deposition was seen on stage 1 with all the devices. The FPF, RF, ED and MMAD values of the four co-SD Fas:Man particles are listed in Table 9.

TABLE 9

In vitro aerosol dispersion performance of co-SD Fas:Man powders at four different pump rates using the FDA-approved human DPI devices, Aerolizer ®, Neohaler ® and Handihaler ® (n = 3, mean ± standard deviation)

|  | Aerolizer | Neohaler | Handihaler |
|---|---|---|---|
|  | Co-SD Fas:Man 25% | | |
| FPF | 7.82 ± 1.79 | 10.81 ± 3.35 | 7.58 ± 0.10 |
| RF | 20.48 ± 9.15 | 25.54 ± 11.47 | 13.00 ± 5.64 |
| ED | 99.09 ± 0.81 | 92.18 ± 0.70 | 101.82 ± 1.77 |
| MMAD | 41.59 ± 22.14 | 11.55 ± 2.72 | 27.81 ± 3.9 |
| GSD | 5.36 ± 1.91 | 2.09 ± 0.34 | 3.05 ± 0.40 |
|  | Co-SD Fas:Man 50% | | |
| FPF | 7.50 ± 0.80 | 3.83 ± 1.27 | 7.44 ± 2.16 |
| RF | 12.80 ± 5.58 | 8.73 ± 4.48 | 11.19 ± 5.53 |
| ED | 94.38 ± 0.54 | 93.42 ± 1.50 | 101.51 ± 6.06 |

TABLE 9-continued

In vitro aerosol dispersion performance of co-SD Fas:Man powders at four different pump rates using the FDA-approved human DPI devices, Aerolizer ®, Neohaler ® and Handihaler ® (n = 3, mean ± standard deviation)

|  | Aerolizer | Neohaler | Handihaler |
|---|---|---|---|
| MMAD | 29.43 ± 1.91 | 30.88 ± 10.32 | 41.58 ± 2.25 |
| GSD | 3.15 ± 0.28 | 2.66 ± 0.57 | 4.75 ± 2.70 |
|  | Co-SD Fas:Man 75% | | |
| FPF | 6.49 ± 0.48 | 5.89 ± 1.19 | 6.32 ± 1.39 |
| RF | 16.27 ± 7.18 | 17.60 ± 8.01 | 10.69 ± 5.00 |
| ED | 99.02 ± 0.87 | 90.92 ± 2.50 | 104.93 ± 1.62 |
| MMAD | 50.81 ± 9.78 | 20.89 ± 5.45 | 35.72 ± 14.48 |
| GSD | 5.71 ± 0.66 | 2.65 ± 0.54 | 3.94 ± 0.29 |
|  | Co-SD Fas:Man 100% | | |
| FPF | 7.90 ± 1.12 | 5.56 ± 1.85 | 6.45 ± 0.86 |
| RF | 19.32 ± 9.20 | 11.67 ± 5.24 | 10.45 ± 4.61 |
| ED | 106.83 ± 16.68 | 91.15 ± 4.41 | 100.09 ± 2.42 |
| MMAD | 31.01 ± 17.13 | 35.17 ± 7.44 | 42.57 ± 5.52 |
| GSD | 5.43 ± 4.00 | 3.42 ± 0.76 | 4.22 ± 0.20 |

The hypothesis of this study was that Man would improve the aerosol performance of Fas when co-SD. In contrast to the individually SD Fas particles at the same pump rate, co-SD particles had a completely different morphology. The elongated particle formation in co-SD Fas: Man samples were similar to the raw Fas. However, on close examination, the smaller nanometer sized particles were seen on the surface which indicates that the particles are indeed smaller and are not the geometrically same size of raw Fas. This was rather a unique particle aggregation since previous studies using Man have all formed spherical particles (X. Li, et al., Journal of pharmaceutical sciences, (2014). However, the stable α-mannitol has shown to form needle-like particles due to high surface energy from confined liquid impinging jet precipitation technique (P. Tang, et al., International journal of pharmaceutics, 367 (2009) 51-57). The diffraction pattern noted in co-SD Fas:Man particles corresponds to that of α-mannitol diffraction peaks from the Cambridge structure database. This could possibly explain the elongated rod like particles of co-SD Fas:Man. It is noted that the co-SD 30:70 molar ratio of Fas:Man was the only successful proportion at which particle formation was possible. Other molar ratios experimented during spray drying includes 90:10 Fas:Man and 50:50 Fas:Man, with no particle formulation. Previously, it was shown that mannitol formed particles with dimethyl fumarate at lower inlet temperature of 90° C. (P. Muralidharan, et al., Molecular Systems Design & Engineering, (2016).), hence the 30:70 molar ratio was spray dried at an inlet temperature of 90° C.

The crystalline peaks of co-SD samples seen in XRPD were consistent with Man peaks observed in earlier studies (X. Li, et al., Journal of pharmaceutical sciences, (2014); P.

Muralidharan, et al., Molecular Systems Design & Engineering, (2016)). This was further confirmed by the DSC and HSM data where melting was seen around 145° C. The single transition (peak) of the co-SD samples seen in DSC and HSM indicate molecular miscibility of Fas and Man at this molar ratio on spray drying. The miscibility is due to hydrogen bonding between mannitol (donor and/or acceptor) and Fas (donor and/or acceptor), which was confirmed from the vibrational stretch seen at 3280 cm$^{-1}$ approximately, on ATR-FTIR spectrum of the sample. The presence of the components in the spray dried sample was confirmed by elemental analysis of EDX where the peaks corresponding to S, O, and Cl were seen. ATR-FTIR and Raman analysis further supported this by showing no change in the spectrum before and after spray drying. The homogenous distribution of Fas in co-SD sample could not be verified using Raman due to the dominance of fluorescence from the co-SD samples. However, the chemical confirmation of the components was established by other techniques. The residual water content was less in the co-SD powders. The inclusion of non-hygroscopic Man as excipient during spray drying further reduced the water content of co-SD samples as previously found (X. Li, et al., Journal of pharmaceutical sciences, (2014)).

Figure 23:
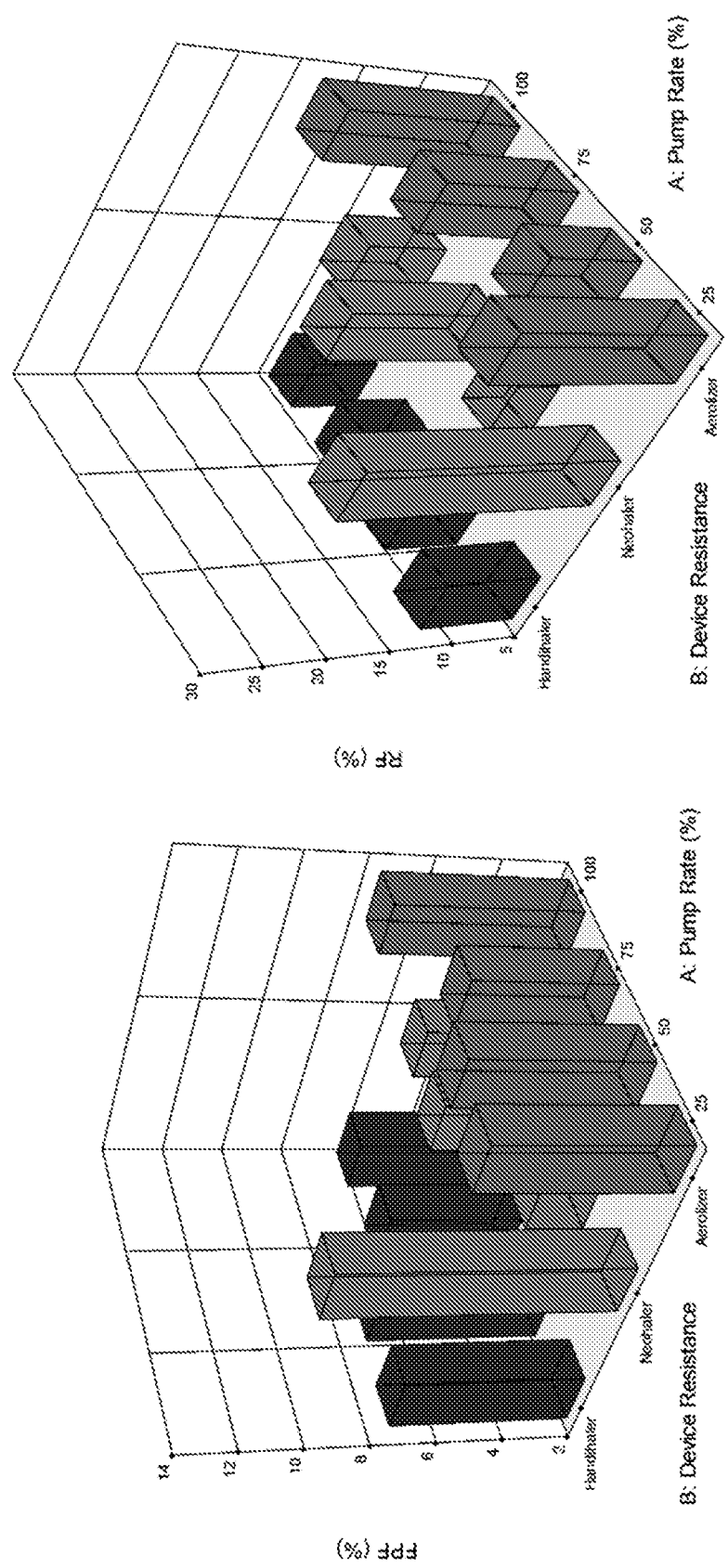
FIG. 23: Design of Experiments 3-D surface plots showing the effect of spray drying pump rate and inhaler device resistance on the aerosol performance of co-SD Fas:Man powders. Plot generated using Design Expert® software.
Figure 23:
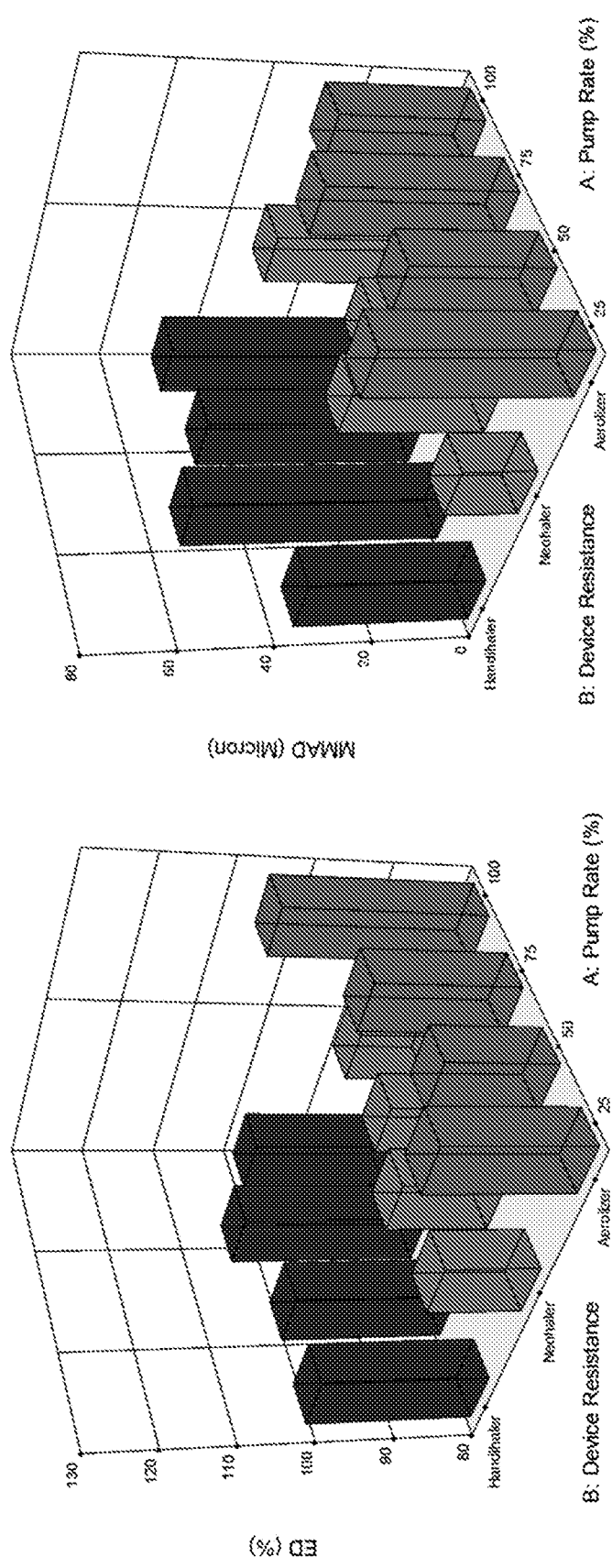

The interaction between the spray drying pump rates and the DPI device resistance is shown in FIGS. 22 and 23. From these plots, it can be seen that the combination of Neohaler® with 25% spray drying pump rate had better FPF, RF, ED and MMAD values compared to the rest of the systems. ANOVA result of the factorial model with pump rate (PR) and device resistance (DR) showed that PR is significant for FPF, DR is significant for ED, MMAD and both PR, DR and the combination of them are significant for RF.

This study successfully produced co-SD Fas:Man particles using spray drying technique at a molar ratio of 30:70 w/w. The comprehensive characterization analysis shows that the particles retained partial crystallinity after spray drying but also exhibited amorphous character due to loss of some crystallinity in the molecular mixture during spray drying. The co-spray dried powder aerosolized with FDA-approved human DPI devices with high emitted doses and exhibited measurable deposition on most stages of the NGI.

All publications and patents mentioned in the present application are herein incorporated by reference. Various modification and variation of the described methods and compositions of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the relevant fields are intended to be within the scope of the following claims.

We claim:

1. A composition, comprising: fasudil (Fas) nanoparticles or microparticles, wherein said nanoparticles or microparticles further comprise a sugar as a pharmaceutically acceptable carrier, wherein the sugar is D-mannitol and said Fas and D-mannitol are present at a molar ratio of 30:70, and wherein said nanoparticles or microparticles are a dry power made by a method, comprising:
    a) preparing a first solution comprising said Fas in methanol;
    b) preparing a second solution comprising said sugar in methanol; and
    c) co-spraying said first and second solutions using a spray drying apparatus.

2. The composition of claim 1, wherein said nanoparticles or microparticles have a diameter of 200 nm to 5 µm.

3. A system, comprising:
    a) the composition of claim 1; and
    b) a dry powder inhaler device.

4. A method of treating a pulmonary disorder in a subject, comprising:
    administering the composition of claim 1 to a subject diagnosed with or having signs or symptoms of a pulmonary disorder such that said signs or symptoms are reduced, wherein said pulmonary disorder is pulmonary hypertension (PH), pulmonary fibrosis, or asthma.

5. The method of claim 4, further comprising administering an additional treatment for PH.

6. The method of claim 5, wherein said additional treatment is selected from the group consisting of a calcium channel blocker, a prostacyclin analogue, a prostacyclin receptor agonist, an endothelin receptor antagonist, a phosphodiesterase type 5 inhibitor, a guanylate cyclase stimulator, an inhaled or systemic corticosteroid, a bronchodilator, and a combination thereof.

7. The method of claim 4, wherein said composition is administered to the lung of said subject using the system of claim 3.

* * * * *

UNITED STATES PATENT AND TRADEMARK OFFICE
CERTIFICATE OF CORRECTION

| | |
|---|---|
| PATENT NO. | : 11,878,023 B2 |
| APPLICATION NO. | : 16/759102 |
| DATED | : January 23, 2024 |
| INVENTOR(S) | : Mansour et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 411 days.

Signed and Sealed this
First Day of July, 2025

Coke Morgan Stewart
*Acting Director of the United States Patent and Trademark Office*